(12) United States Patent
Murakami et al.

(10) Patent No.: US 12,180,404 B2
(45) Date of Patent: Dec. 31, 2024

(54) LIGHT-EMITTING BODY, METHOD FOR PRODUCING LIGHT-EMITTING BODY, AND BIOLOGICAL MATERIAL LABELING AGENT

(71) Applicant: Murata Manufacturing Co., Ltd., Nagaokakyo (JP)

(72) Inventors: Takayoshi Murakami, Nagaokakyo (JP); Norikazu Fujihira, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 598 days.

(21) Appl. No.: 17/507,055

(22) Filed: Oct. 21, 2021

(65) Prior Publication Data

US 2022/0041929 A1 Feb. 10, 2022

Related U.S. Application Data

(63) Continuation of application No. PCT/JP2020/020608, filed on May 25, 2020.

(30) Foreign Application Priority Data

Jun. 4, 2019 (JP) .................................. 2019-104508

(51) Int. Cl.
*C09K 11/88* (2006.01)
*B82Y 20/00* (2011.01)
(Continued)

(52) U.S. Cl.
CPC ............ *C09K 11/88* (2013.01); *C01G 15/006* (2013.01); *G01N 33/582* (2013.01); *G01N 33/68* (2013.01);
(Continued)

(58) Field of Classification Search
CPC ...... C09K 11/88; G01N 33/582; G01N 33/68; B82Y 20/00; B82Y 40/00; C01P 2004/64; C01P 2006/60
(Continued)

(56) References Cited

U.S. PATENT DOCUMENTS

2009/0159849 A1 6/2009 Uehara et al.
2016/0115378 A1 4/2016 Ezure
2018/0291267 A1 10/2018 Nagano et al.

FOREIGN PATENT DOCUMENTS

CN 104445098 A 3/2015
CN 105154084 A 12/2015
(Continued)

OTHER PUBLICATIONS

CN 104445098 A English translation (Year: 2015).*
(Continued)

*Primary Examiner* — Anita Nassiri-Motlagh
(74) *Attorney, Agent, or Firm* — ArentFox Schiff LLP

(57) ABSTRACT

A dispersion that includes water and a light-emitting body dispersed in the water. The light-emitting body contains a nanoparticle of a AgInSe compound semiconductor, and a film to which hydrophilicity is imparted by ultrasonic irradiation on a surface of the nanoparticle. The film has a double structure having a first organic molecular film containing an alkylthiol and a second organic molecular film composed mainly of a fatty acid. The light-emitting body has an emission quantum yield of 10% or more, an emission intensity peak wavelength in the range of 650 to 1000 nm, and a half-width ΔH of 100 nm or less at the emission intensity peak wavelength.

21 Claims, 17 Drawing Sheets

(51) Int. Cl.
  *B82Y 40/00* (2011.01)
  *C01G 15/00* (2006.01)
  *G01N 33/58* (2006.01)
  *G01N 33/68* (2006.01)

(52) U.S. Cl.
  CPC .......... *B82Y 20/00* (2013.01); *B82Y 40/00* (2013.01); *C01P 2004/64* (2013.01); *C01P 2006/60* (2013.01)

(58) Field of Classification Search
  USPC .................................................. 252/301.4 R
  See application file for complete search history.

(56) References Cited

FOREIGN PATENT DOCUMENTS

| JP | 2007169605 A | 7/2007 |
| JP | 2016176039 A | 10/2016 |
| WO | 2009054244 A1 | 4/2009 |
| WO | 2014196319 A1 | 12/2014 |
| WO | 2017126164 A1 | 7/2017 |

OTHER PUBLICATIONS

CN 105154084 A English translation (Year: 2015).*
Written Opinion of the International Searching Authority issued for PCT/JP2020/020608, date of mailing Aug. 18, 2020.
M.Z. Fahmi et al.; "Forming double layer-encapsulated quantum dots for bio-imaging and cell targeting"; Nanoscale, 2013, 5, pp. 1517-1528.
International Search Report issued for PCT/JP2020/020608, date of mailing Aug. 18, 2020.

* cited by examiner

Fig. 5(a)
Fig. 5(b)
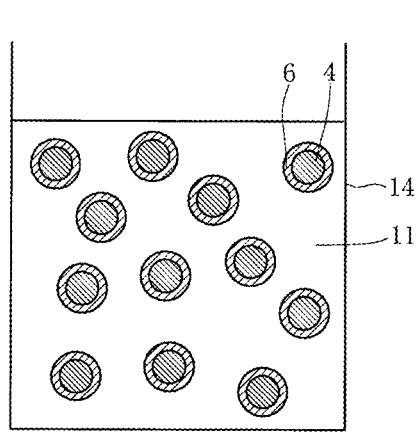
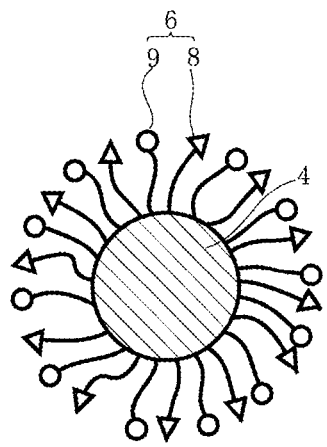
Fig. 6
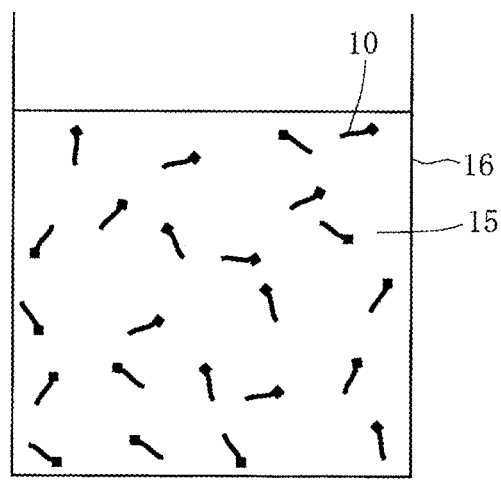

LIGHT-EMITTING BODY, METHOD FOR PRODUCING LIGHT-EMITTING BODY, AND BIOLOGICAL MATERIAL LABELING AGENT

CROSS REFERENCE TO RELATED APPLICATIONS

The present application is a continuation of International application No. PCT/JP2020/020608, filed May 25, 2020, which claims priority to Japanese Patent Application No. 2019-104508, filed Jun. 4, 2019, the entire contents of each of which are incorporated herein by reference.

FIELD OF THE INVENTION

The present invention relates to a dispersion containing a light-emitting body, a method for producing the dispersion, and a biological material labeling agent, and more particularly to a dispersion containing a light-emitting body suitable for labeling (biomarker) of a biological material constituting a living body.

BACKGROUND OF THE INVENTION

In recent years, in the biomedical field, attention has been given to bioimaging technology that provides fluorescence to a biological material to dynamically analyze an image with high sensitivity and with multiple colors and examine the effects of medication and the state of cells in regenerative medicine, cancer therapy, and the like. In this bioimaging technology, a light-emitting body composed of ultrafine semiconductor nanoparticles is adsorbed on a biological tissue and is irradiated with light to emit light for detecting biological information. Thus, only light irradiation of the light-emitting body in a living body can determine the state of a biological material and is expected to be a simpler and safer medical examination than positron emission tomography (PET) and computed tomography (CT).

In this type of bioimaging technology, it is conventionally preferable to use a light-emitting body that causes a fluorescent phenomenon in the near-infrared region in the wavelength range of 700 to 1700 nm. More specifically, biological constituents, such as hemoglobin, have higher absorption in the visible light region in the wavelength of 400 nm or more and less than 700 nm, i.e., shorter than the wavelength in the near-infrared region. At a wavelength of more than 1700 nm, due to large absorption by water, light cannot efficiently pass through a living body. In contrast, the near-infrared region in the wavelength range of 700 to 1700 nm, particularly a region in the wavelength range of 700 to 1000 nm, has high light transmittance in a living body and is considered to be suitable for bioimaging technology.

Semiconductor nanoparticles have been extensively studied and developed in various technical fields. In particular, compound semiconductors with a chalcopyrite crystal structure composed of elements of the I-III-VI group are direct band gap semiconductors that emit light due to recombination of electrons and holes by light absorption, that contain no harmful elements, such as Cd, that have low toxicity, and that have low environmental load, and are therefore considered to be new promising functional materials.

For example, Patent Document 1 proposes a light-emitting body that is formed of nanoparticles of a compound semiconductor containing a Ag component, an In component, and a Se component, has an emission intensity peak wavelength in the range of 700 to 1400 nm, and has a half-width $\Delta H$ of 100 nm or less at the peak wavelength.

In Patent Document 1, nanoparticles of a AgInSe compound semiconductor are dispersed in a nonpolar solvent, such as chloroform, by using a solvent, such as 1-dodecanethiol or oleylamine. According to an example of Patent Document 1, the emission intensity peak wavelength can be controlled in the range of 700 to 1000 nm, the half-width $\Delta H$ at the peak wavelength is as small as 100 nm or less, and good emission properties can be achieved. Furthermore, the emission quantum yield as an indicator of luminous efficiency is maximum when the blend ratio of Ag to In, that is, the Ag/In ratio is ½, and reaches 12%.

Non Patent Document 1 reports the formation of double-layer encapsulated quantum dots (DL-Qdots) for bioimaging and cell targeting.

In Non Patent Document 1, first, $AgInS_2/ZnS$ quantum dots (nanoparticles) covered with an organic ligand derived from a solvent, such as 1-dodecanethiol or octadecene, are synthesized using the solvent, and are dispersed in a nonpolar solvent hexane to prepare a dispersion liquid. A lauric acid (dodecanoic acid) solution is then added to the dispersion liquid to produce a phase-separated solution of a hexane phase and an aqueous phase. Ultrasonic waves are then applied to the phase-separated solution to cover the surface of each $AgInS_2/ZnS$ quantum dot with an organic ligand derived from the solvent and with an alkyl-capping ligand derived from lauric acid, thereby forming quantum dots with hydrophilicity (Non Patent Document 1, Scheme 1).

It is described in Non Patent Document 1 that before and after the ultrasonic wave irradiation the emission intensity peak wavelength is 550 nm, and there are no large variations in the half-width $\Delta H$ (Non Patent Document 1, FIG. 3). The emission quantum yield is 78% before ultrasonic irradiation but is decreased to 27.7% after the ultrasonic irradiation when the alkyl-capping ligand is formed using lauric acid. It has also been reported that even when the alkyl-capping ligand is formed using a fatty acid other than lauric acid, the emission quantum yield is significantly decreased after hydrophilization (Non Patent Document 1, FIG. 4).

A light-emitting body containing silicon nanoparticles as a light-emitting material to emit light in the near-infrared region has also been developed.

For example, Patent Document 2 proposes water-soluble silicon nanoparticles that contain one or more silicon nanocrystals with a diamond structure, a hydrocarbon film covering the surface of each silicon nanocrystal, and a block copolymer covering one or more silicon nanocrystals covered with the carbon hydrogen film and that emit light in the near-infrared region upon excitation light irradiation.

In Patent Document 2, water-soluble silicon nanoparticles with a half-width $\Delta H$ in the range of 150 to 300 nm and an emission quantum yield of 30% or more in the near-infrared region of 700 to 1000 nm are formed by adjusting the particle size of silicon nanocrystals.

Patent Document 1: International Publication WO 2017/126164 (Claims 1 and 7, paragraphs [0066] to [0073], [0090] to [0100], [0107] to [0112], Table 1, etc.)

Patent Document 2: Japanese Unexamined Patent Application Publication No. 2016-176039 (Claim 1, FIG. 5, etc.)

Non Patent Document 1: M. Z. Fahmi et al., "Forming double layer-encapsulated quantum dots for bio-imaging and cell targeting", Nanoscale, 2013, 5, pp. 1517-1528

SUMMARY OF THE INVENTION

However, in Patent Document 1, there are problems as described below, though a good emission spectrum with a half-width $\Delta H$ of 100 nm or less in the near-infrared region was obtained.

In the field of bioimaging, as described above, a light-emitting body of nanoparticles adsorbed on a biological tissue emits light for detecting biological information. Nanoparticles in Patent Document 1 are dispersed in a nonpolar organic solvent. Thus, the nonpolar organic solvent that is harmful to cells is adsorbed on biological constituents. This is not suitable for a cell-targeting light-emitting body for bioimaging.

In Non Patent Document 1, although $AgInS_2/ZnS$ quantum dots to which hydrophilicity is imparted by ultrasonic irradiation are formed, the emission intensity peak wavelength is 550 nm, and light is emitted in the visible light region. The possible reason for this is described below.

Unlike $AgInSe_2$ in Patent Document 1, $AgInS_2$ has a large band-gap energy of 1.87 eV (660 nm in wavelength) in the bulk state, and the band-gap energy increases due to the quantum size effect when particles are nano-sized. This facilitates light emission in the visible light region. Furthermore, in Non Patent Document 1, ZnS with a large band-gap energy of 3.91 eV (317 nm in wavelength) is injected into AgInSe quantum dots. Although ZnS contributes to surface passivation, the emission wavelength shifts to the short wavelength side due to the large band-gap energy, as described above, and therefore light is emitted in the visible light region of 550 nm.

Thus, light is emitted in the visible light region in Non Patent Document 1, and absorption by biological constituents, such as hemoglobin, is increased. Thus, an image cannot be precisely analyzed, and desired biological information is difficult to obtain. Furthermore, in the $AgInS_2/ZnS$ quantum dots, the emission quantum yield is much lower after ultrasonic irradiation than before the ultrasonic irradiation, resulting in lower luminous efficiency.

Although a light-emitting body in Patent Document 2 emits light at an emission quantum yield of 30% or more in the near-infrared region, the half-width ΔH at the peak wavelength is as large as 150 to 300 nm. This results in poor resolution, and desired precise biological information may not be obtained.

In view of such situations, it is an object of the present invention to provide a light-emitting body that has high luminous efficiency, emits strong light in a near-infrared region, can detect much biological information, has low toxicity, and is suitable for bioimaging; a method for producing the light-emitting body; and a biological material labeling agent containing the light-emitting body.

As described above, AgInSe compound semiconductors have lower toxicity than Cd compound semiconductors, and nanoparticles of AgInSe compound semiconductors can provide a light-emitting body having a peak wavelength with a small half-width ΔH in a desired near-infrared region.

As described above, however, nanoparticles in Patent Document 1 are dispersed in a nonpolar organic solvent, such as chloroform. When such nanoparticles are used in a biological material labeling agent, an organic solvent harmful to cells will be adsorbed on a biological tissue, which is unfavorable as a light-emitting body for bioimaging.

Thus, the present inventors have conducted extensive studies. An alkylthiol, such as 1-dodecanethiol, was coordinated to the surface of nanoparticles of a AgInSe compound semiconductor. An aqueous solution of a fatty acid, such as oleic acid, with a plurality of alkyl groups was then mixed with a dispersion liquid containing nanoparticles dispersed in a nonpolar organic solvent to prepare a phase-separated solution. Ultrasonic irradiation were applied to the phase-separated solution to form a film with hydrophilicity on the surface of the nanoparticles. The emission spectrum and emission quantum yield of the nanoparticles were measured. It was found that the emission intensity peak wavelength and half-width were unchanged by ultrasonic irradiation, the emission quantum yield could be 10% or more, preferably 30% or more, and the luminous efficiency could be improved without degradation of emission spectral characteristics. Furthermore, the hydrophilicity of the film enables a light-emitting body with good emission spectral characteristics and high luminous efficiency to be dispersed in water. Thus, the light-emitting body can be low-toxic and suitable for bioimaging.

The present invention is based on such findings. A dispersion according to an aspect of the present invention contains water and a light-emitting body dispersed in the water. The light-emitting body contains a nanoparticle of a compound semiconductor containing at least a Ag component, an In component, and a Se component, and a film with hydrophilicity on the surface of the nanoparticle, the light-emitting body has an emission quantum yield of 10% or more.

The light-emitting body preferably has an emission quantum yield of 50% or less.

The light-emitting body preferably has an emission intensity peak wavelength in the range of 650 to 1000 nm and a half-width of 100 nm or less at the emission intensity peak wavelength.

Thus, it is possible to provide a light-emitting body with high resolution in the near-infrared region, with hydrophilicity, and with high luminous efficiency without degradation of emission spectral characteristics.

A dispersion according to an aspect of the present invention contains water and a light-emitting body dispersed in the water, where the light-emitting body contains a nanoparticle of a compound semiconductor containing at least a Ag component, an In component, and a Se component, and a film with hydrophilicity on the surface of the nanoparticle, the light-emitting body has an emission intensity peak wavelength in the range of 650 to 1000 nm and a half-width of 100 nm or less at the emission intensity peak wavelength.

Thus, even when hydrophilicity is imparted to the surface of each nanoparticle, it is possible to provide a light-emitting body with a good half-width and high resolution in the near-infrared region, with good emission spectral characteristics, and suitable for bioimaging.

The light-emitting body preferably has an emission quantum yield in the range of 10% to 50%.

Thus, it is possible to provide a high-performance light-emitting body with hydrophilicity that has both good emission spectral characteristics and high luminous efficiency.

In a dispersion according to an aspect of the present invention, as described above, an alkylthiol is coordinated to the surface of nanoparticles, a dispersion liquid containing the nanoparticles dispersed in a nonpolar solvent is mixed with a fatty acid aqueous solution to prepare a phase-separated solution, and the phase-separated solution is subjected to ultrasonic irradiation. Thus, the film has hydrophilicity due to the ultrasonic irradiation, has a double structure having a first organic molecular film containing the alkylthiol and a second organic molecular film composed mainly of the fatty acid, and is formed at a high density on the surface of the nanoparticles.

In a dispersion according to an aspect of the present invention, preferably, the film has a double structure having a first organic molecular film containing at least an alkylthiol and a second organic molecular film composed mainly of a fatty acid with a plurality of alkyl groups, and the hydrophilicity is imparted by ultrasonic irradiation.

This results in the formation of a high-density film, which can effectively cap a surface defect of the nanoparticles. Unlike imparting hydrophilicity by a ligand substitution reaction, imparting hydrophilicity by ultrasonic irradiation can prevent the formation of a new surface defect. Thus, it is possible to provide a light-emitting body that has high luminous efficiency with an emission quantum yield of 10% or more, has both hydrophilicity and high luminous efficiency, and is suitable for bioimaging.

In the dispersion according to the present invention, preferably, the alkylthiol is 1-dodecanethiol, and the fatty acid is oleic acid.

Furthermore, according to the present invention, the alkyl groups of the fatty acid preferably have a longer chain length than the alkyl group of the alkylthiol.

Thus, the chain length of the alkyl groups can be adjusted to have higher luminous efficiency.

In the dispersion according to the present invention, the first organic molecular film preferably contains a surface protective agent containing n-octyl thioglycolate or 1-dodecanethiol.

A desired surface protective agent for protecting the surface of the nanoparticles can be selected as required to adjust the emission intensity peak wavelength in the near-infrared region in the range of 650 to 1000 nm.

Furthermore, the light-emitting body preferably has luminous efficiency with an emission quantum efficiency of 30% or more.

In the dispersion according to the present invention, preferably, the nanoparticles contain a Ga component, and the peak wavelength is controlled in accordance with the Ga component content.

Thus, the emission intensity peak wavelength can also be controlled without degradation of the half-width or luminous efficiency by containing the Ga component in the nanoparticles and changing the Ga component content.

The light-emitting body preferably has a transmittance of 90% or more in the wavelength range of 1000 to 1100 nm.

At a transmittance of 90% or more in the wavelength range of 1000 to 1100 nm, the nanoparticles are dispersed in water as ultrafine particles without aggregation.

In the present invention, the In component is preferably contained in a larger amount than the stoichiometric composition.

Such an In-rich composition can prevent a nonradiative deactivation process in an absorption-emission process and can provide better emission properties.

Furthermore, the present inventors have conducted extensive studies, have examined the applicability of such a light-emitting body containing nanoparticles as a light source to a biological material labeling agent, and have found that the light-emitting body can be efficiently introduced into a biological material by covering the film with a surface modifier containing a cell-penetrating peptide, such as cationic octaarginine (hereinafter referred to as "R8"), as a main component.

Thus, according to the present invention, the film is preferably covered with a surface modifier composed mainly of a cationic cell-penetrating peptide.

Thus, the surface modifier in the light-emitting body is positively charged, and the light-emitting body is attracted by a negatively charged cell membrane and moves to the surface of a biological material. Then, the light-emitting body can be easily introduced into the biological material by endocytosis and can only be irradiated with light to efficiently detect biological information.

In the present invention, the cell-penetrating peptide is preferably R8.

In the light-emitting body, the nanoparticles serving as a light source are formed of a AgInSe compound semiconductor, as described above. Thus, the light-emitting body has lower toxicity than compound semiconductors containing Cd and can contribute to an improvement in cell survival rate when introduced into a biological material.

Thus, the present inventors have conducted further extensive studies using adipose-derived stem cells (hereinafter referred to as ""ASCs""), which have recently attracted attention in regenerative medicine and the like, and have found that the light-emitting body introduced into ASCs at 160 nmol/L on a molar concentration basis can have a cell survival rate of 80% or more.

Thus, the light-emitting body according to the present invention introduced into ASCs at 160 nmol/L on a molar concentration basis preferably has a cell survival rate of 80% or more.

Thus, the light-emitting body introduced into ASCs even at a high concentration of 160 nmol/L on a molar concentration basis causes less cell death, can successfully maintain the cell survival rate, and can acquire more biological information.

A method for producing a dispersion according to the present invention includes preparing a nonpolar nanoparticle dispersion liquid in which nanoparticles of a compound semiconductor containing at least a Ag component, an In component, and a Se component are dispersed in a nonpolar solvent; preparing a precursor dispersion liquid by adding organic molecules including at least an alkylthiol to the nonpolar nanoparticle dispersion liquid to form a first organic molecular film on a surface of each nanoparticle; preparing a fatty acid aqueous solution in which a fatty acid with a plurality of alkyl groups is dissolved in water in the presence of an alkali; mixing the precursor dispersion liquid and the fatty acid aqueous solution to prepare a phase-separated solution containing a nonpolar solvent phase and an aqueous phase; applying ultrasonic waves to the phase-separated solution to form a film with hydrophilicity on a surface of each nanoparticle; and dispersing the nanoparticles in water to prepare an aqueous nanoparticle dispersion.

Thus, the organic molecules including at least an alkylthiol are added to the nonpolar nanoparticle dispersion liquid to adsorb a thiol group of the alkylthiol on a surface defect of the nanoparticles and form the first organic molecular film on the surface of the nanoparticles, thereby producing the precursor dispersion liquid. The precursor dispersion liquid and the fatty acid aqueous solution are then mixed to prepare the phase-separated solution. Ultrasonic waves are applied to the phase-separated solution to adsorb the alkyl groups of the fatty acid on the surface of the nanoparticles by hydrophobic interaction with the alkyl group of the alkylthiol. The carboxy group, which is a hydrophilic group, of the fatty acid imparts hydrophilicity to the film. Thus, the light-emitting body can be dispersed in water in the phase-separated solution, which is phase-separated again after ultrasonic irradiation. Thus, the light-emitting body can have good emission spectral characteristics and high luminous efficiency.

In the method for producing a dispersion according to the present invention, the forming of the film on the surface of each nanoparticle preferably includes forming an oil-in-water microemulsion by the ultrasonic irradiation so as to confine the nanoparticles with the first organic molecular film formed thereon and the fatty acid in the microemulsion to adsorb the fatty acid on the surface of each nanoparticle.

The ultrasonic irradiation applies a large impact force to the microemulsion and gradually decreases the size of the microemulsion with the lapse of irradiation time. The fatty acid adsorbed on the surface of the nanoparticles is self-organized to form a second organic molecular film. This, together with the imparted hydrophilicity, enables the light-emitting body to be dispersed in water after the ultrasonic irradiation.

In the method for producing a dispersion according to the present invention, the preparing of the nonpolar nanoparticle dispersion liquid preferably includes: dissolving a Ag compound and an In compound in a solvent to prepare a Ag—In solution; dissolving a Se powder in a solvent to prepare a Se solution; injecting the Se solution into the Ag—In solution while the Ag—In solution is heated to a predetermined temperature to prepare a mixed solution; and heating the mixed solution at a reaction temperature higher than the predetermined temperature for a predetermined reaction time to produce a nanoparticle of a compound semiconductor covered with a surface protective agent. Furthermore, the preparing of the nonpolar nanoparticle dispersion liquid preferably includes: dissolving a Ag compound, an In compound, and a Ga compound in a solvent to prepare a Ag—In—Ga solution; dissolving a Se powder in a solvent to prepare a Se solution; injecting the Se solution into the Ag—In solution while the Ag—In solution is heated to a predetermined temperature to prepare a mixed solution; and heating the mixed solution at a reaction temperature higher than the predetermined temperature for a predetermined reaction time to produce a nanoparticle of a compound semiconductor covered with a surface protective agent.

Producing the compound semiconductor at the predetermined temperature followed by heating at a reaction temperature higher than the predetermined temperature for the predetermined reaction time in this manner minimizes aggregation of the nanoparticles, improves the crystallinity of the nanoparticles, and decreases energy loss. Thus, a light-emitting body capable of band-edge luminescence can be efficiently produced.

The method for producing a dispersion according to the present invention preferably further includes mixing the nanoparticles with the film formed thereon and a surface modifier composed mainly of a cationic cell-penetrating peptide so as to cover the surface of the film with the cell-penetrating peptide, and the cell-penetrating peptide is preferably octaarginine.

Thus, the light-emitting body can be easily introduced into a biological material, as described above.

A biological material labeling agent according to the present invention includes the light-emitting body dispersed in water.

Thus, the light-emitting body has hydrophilicity, good emission spectral characteristics, and high luminous efficiency. A biological image can therefore be dynamically and efficiently analyzed with desired high sensitivity, with multiple colors, and without adsorption of a harmful substance, such as an organic solvent, on a biological tissue, and a biological material labeling agent suitable for a biomarker for bioimaging can be produced. In particular, when the film is covered with a surface modifier composed mainly of a cationic (positively charged) cell-penetrating peptide, electrostatic interaction occurs between a negatively charged cell membrane and the cationic (positively charged) cell-penetrating peptide. Thus, after the light-emitting body moves to the surface of the cell membrane, the light-emitting body can be easily introduced into a biological material by endocytosis and can effectively label the biological material.

Thus, only light irradiation of the light-emitting body introduced into the biological material can determine the state of the biological material.

The light-emitting body according to an aspect of the present invention has high luminous efficiency suitable for bioimaging without adsorption of a nonpolar organic solvent harmful to cells on a biological tissue can be produced.

The light-emitting body according to another aspect of the present invention has, even when the surface of the nanoparticle is made hydrophilic, good emission spectral characteristics with high resolution without an increase in half-width in the near-infrared region and is suitable for bioimaging.

Furthermore, as noted above, the method for producing the dispersion according to an aspect of the present invention includes preparing a nonpolar nanoparticle dispersion liquid in which nanoparticles of a compound semiconductor containing at least a Ag component, an In component, and a Se component are dispersed in a nonpolar solvent, adding organic molecules including at least an alkylthiol to the nonpolar nanoparticle dispersion liquid to form a first organic molecular film on a surface of each nanoparticle and prepare a precursor dispersion liquid, preparing a fatty acid aqueous solution in which a fatty acid with a plurality of alkyl groups is dissolved in water in the presence of an alkali, mixing the precursor dispersion liquid and the fatty acid aqueous solution to prepare a phase-separated solution containing a nonpolar solvent phase and an aqueous phase, applying ultrasonic waves to the phase-separated solution to form a film with hydrophilicity on a surface of each nanoparticle, and dispersing the nanoparticles in water to prepare an aqueous nanoparticle dispersion. Thus, first, the thiol group of the alkylthiol is adsorbed on a surface defect of the nanoparticles to form the first organic molecular film on the surface of the nanoparticles, and the precursor dispersion liquid is prepared. The precursor dispersion liquid and the fatty acid aqueous solution are then mixed to prepare the phase-separated solution. Ultrasonic waves are applied to the phase-separated solution to adsorb the alkyl groups of the fatty acid on the surface of the nanoparticles by hydrophobic interaction with the alkyl group of the alkylthiol. The carboxy group, which is a hydrophilic group, of the fatty acid imparts hydrophilicity to the film and, in the phase-separated solution, which is phase-separated again after ultrasonic irradiation, the nanoparticles with the hydrophilic film formed thereon move to the aqueous phase side and are dispersed in water. Thus, the light-emitting body can have good emission spectral characteristics and high luminous efficiency.

The biological material labeling agent according to an aspect of the present invention allows a biological image to be dynamically and efficiently analyzed with desired high sensitivity, with multiple colors, and without adsorption of a harmful substance, such as an organic solvent, on a biological tissue, and a biological material labeling agent with low toxicity suitable for a biomarker for bioimaging. In particular, when the film is covered with a surface modifier composed mainly of a cationic (positively charged) cell-penetrating peptide, electrostatic interaction occurs between a negatively charged cell surface and the cationic (positively charged) cell-penetrating peptide. Thus, the light-emitting body can be easily introduced into a cell of a biological material and can effectively label the biological material. Thus, only light irradiation of the light-emitting body introduced into a living body can determine the state of the biological material.

BRIEF DESCRIPTION OF THE DRAWINGS

FIGS. 5(a) and 5(b) are process drawings (2/6) for explaining one embodiment of a method for producing a light-emitting body according to the present invention.

FIG. 6 is a process drawing (3/6) for explaining one embodiment of a method for producing a light-emitting body according to the present invention.

DETAILED DESCRIPTION OF THE PREFERRED EMBODIMENTS

Next, embodiments of the present invention are described in detail.

<Light-Emitting Body and Method for Producing the Light-Emitting Body>

First Embodiment

Figure 1:
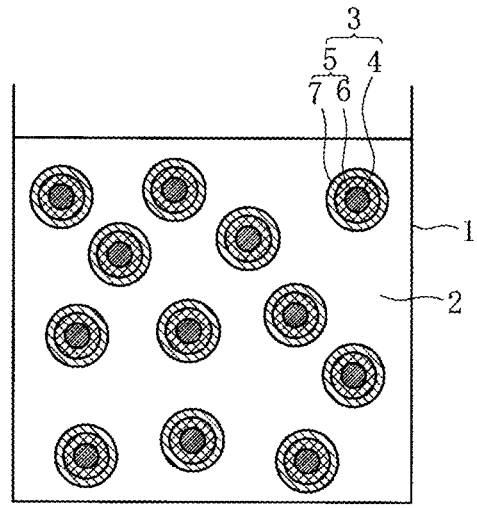
FIG. 1 is a schematic view of a light-emitting body according to the present invention dispersed in water.

FIG. 1 is a schematic view of a light-emitting body according to an embodiment (first embodiment) of the present invention dispersed in water.

A container 1 contains water 2, and a light-emitting body 3 is dispersed in the water. More specifically, the light-emitting body 3 has a transmittance of 90% or more in the wavelength range of 1000 to 1100 nm in a transmission spectrum and has a good dispersion state in water without aggregation or the like.

The light-emitting body 3 contains a nanoparticle 4 of a AgInSe compound semiconductor containing a Ag component, an In component, and a Se component, and a film 5 to which hydrophilicity is imparted by ultrasonic irradiation is on the surface of the nanoparticle 4. The film 5 has a double structure having a first organic molecular film 6 containing at least an alkylthiol and a second organic molecular film 7 composed mainly of a fatty acid with a plurality of alkyl groups.

The light-emitting body 3 has an emission quantum yield of 10% or more, preferably 30% or more, and has emission spectral characteristics satisfying an emission intensity peak wavelength in the range of 650 to 1000 nm and a half-width $\Delta H$ of 100 nm or less at the peak wavelength.

In the light-emitting body 3, hydrophilicity is imparted to the film 5 by ultrasonic irradiation, and the film 5 has a double structure. Thus, the film 5 has a high density and satisfactorily caps a surface defect, and therefore the emission quantum yield can be 10% or more, preferably 30% or more. Furthermore, the film 5 has hydrophilicity and can be used in a dispersed state in water. Thus, the light-emitting body 3 can have both good emission spectral characteristics and high luminous efficiency without adsorption of a non-polar organic solvent harmful to cells on a biological tissue and is suitable for bioimaging.

Next, the reasons for the nanoparticle material, emission spectral characteristics (emission intensity peak wavelength and half-width $\Delta H$), and emission quantum yield defined as described above in the present embodiment are described below in detail.

(1) Nanoparticle Material

As described above, unlike Cd materials, such as CdSe and CdTe, a AgInSe semiconductor compound with a chalcopyrite crystal structure has low toxicity, and the emission wavelength can be controlled by adjusting the composition and forming a solid solution. Furthermore, a AgInSe semiconductor compound, for example, $AgInSe_2$ has a small band-gap energy of 1.24 eV (1000 nm wavelength) in the bulk state and emits light in the near-infrared region. Thus, when the particle size of a AgInSe semiconductor compound is controlled on the order of nanometers, due to the quantum size effect, the AgInSe semiconductor compound even with the same composition emits light at various wavelengths in the near-infrared region.

Thus, in the present embodiment, a AgInSe compound semiconductor is used as a nanoparticle material serving as a core of the light-emitting body 3.

Although the AgInSe compound semiconductor may have any component ratio at which emission spectral characteristics are not impaired, the In component content is preferably higher than the stoichiometric composition.

More specifically, although the stoichiometric composition of the Ag component and the In component is 1:1, a higher In component content than the stoichiometric composition in production can result in the prevention of the nonradiative deactivation process, in which excited electrons returning to the ground state emit no light, and can result in an emission peak with improved intensity. However, a much higher In component than the stoichiometric composition in production may result in the formation of impurities, such as a different phase, and consequently low purity, thus resulting in a decrease in emission peak intensity. In view of such a point, when the In component content in production is higher than the stoichiometric composition, the blend ratio of the In component to the Ag component preferably ranges from 1.5 to 3 in terms of mole ratio.

The nanoparticles 4 may have any average particle size, provided that the quantum size effect is produced in the wavelength range of 650 to 1000 nm. For example, the average particle size ranges from 0.1 to 20 nm.

(2) Emission Spectral Characteristics (Emission Intensity Peak Wavelength and Half-Width $\Delta H$)

Figure 2:
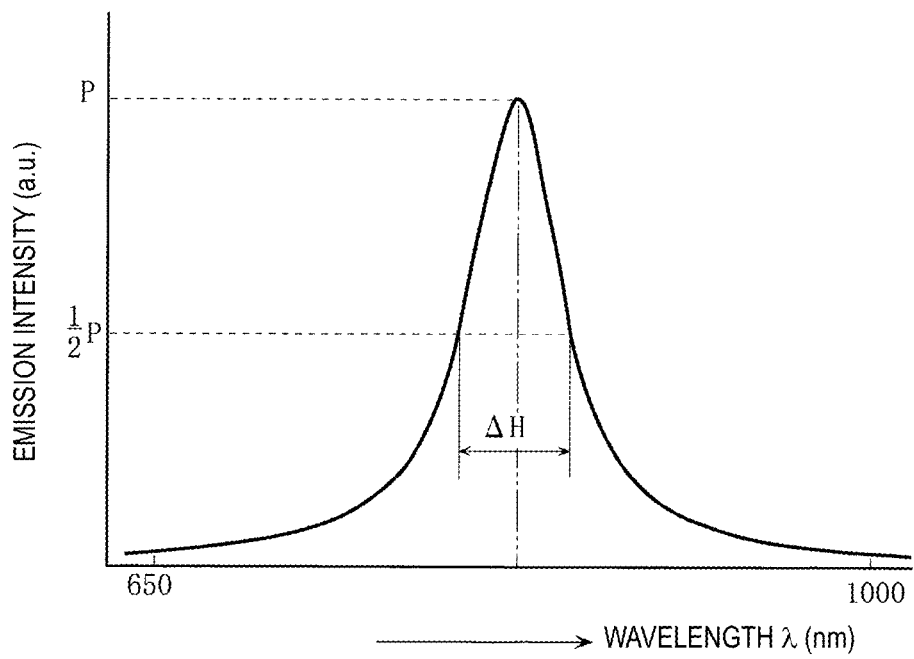
FIG. 2 is a profile of a principal part of an emission spectrum of the light-emitting body.

FIG. 2 is a schematic profile of a principal part of the emission spectrum of the light-emitting body 3. The horizontal axis represents the wavelength (nm), and the vertical axis represents the emission intensity (a.u.).

As described above, a biological constituent, such as hemoglobin, has large absorption in a visible light region of less than 700 nm, particularly less than 650 nm, which is shorter than near-infrared. On the other hand, at a wavelength of more than 1700 nm, absorption by water increases, and therefore light cannot efficiently pass through a living body. Thus, desired biological information is difficult to acquire even when light is emitted in the living body.

In contrast, due to high light transmittance in a living body, the near-infrared region in the wavelength range of 700 to 1700 nm is suitable for dynamic image analysis of a biological tissue utilizing bioimaging technology. In particular, light transmittance in a living body is high in the wavelength range of 650 to 1000 nm, and an emission spectrum in which the emission intensity has a peak wavelength in such a range can be measured to acquire desired biological information.

Furthermore, to acquire desired biological information using bioimaging technology, the light-emitting body 3 needs to emit strong light to enhance resolution. To this end, a profile near the peak wavelength of the emission spectrum should be steep and sharp. The steepness and sharpness of the peak wavelength can be evaluated by the wavelength width at 1/2P of the emission intensity peak wavelength P, that is, the half-width $\Delta H$. More specifically, a half-width $\Delta H$ of more than 100 nm may result in the lack of the steepness and sharpness of the peak wavelength and a decrease in resolution.

Thus, in the present embodiment, the emission intensity peak wavelength is defined in the range of 650 to 1000 nm, and the half-width $\Delta H$ at the peak wavelength is defined in the range of 100 nm or less. Although the half-width $\Delta H$ has no particular lower limit, an excessively small half-width $\Delta H$ tends to result in a "deviation" from the target, and accurate biological information may not be detected. Thus, the lower limit is preferably 10 nm or more.

Thus, in the present embodiment, the emission intensity peak wavelength and half-width $\Delta H$ can be defined as described above to produce a light-emitting body suitable for a biomarker for bioimaging that examines the effects of medication and the state of cells in regenerative medicine, cancer therapy, and the like. Thus, it is possible to provide fluorescence to a biological material to dynamically analyze an image with high sensitivity and with multiple colors.

(3) Emission Quantum Yield

The nanoparticle 4 is an ultrafine particle on the order of nanometers and has a large number of atoms on its surface. Thus, there are many surface defects, which prevent light emission and decrease luminous efficiency, and a sufficient emission quantum yield (the proportion of photons released by light emission among photons absorbed by the nanoparticle) cannot be achieved.

Thus, focusing on the coordination power of organic solvents, it has been attempted to dissolve a nanoparticle material in an organic solvent, cover the surface with a surface protective agent composed of an organic ligand simultaneously with the synthesis of the nanoparticle 4, capping surface defects and removing the surface defects as much as possible, and thereby improve the emission quantum yield.

However, a technique for removing surface defects with a surface protective agent has its limits, and therefore the emission quantum yield cannot be sufficiently improved only by capping with the surface protective agent.

Thus, in the present embodiment, after the synthesis of the nanoparticle 4, the first organic molecular film 6 is formed with organic molecules containing at least an alkylthiol on the surface of the nanoparticle to further decrease surface defects, and then the second organic molecular film 7 composed mainly of a fatty acid is formed on the surface of the nanoparticle 4 by ultrasonic irradiation, thereby forming the film 5 with a double structure composed of the first organic molecular film 6 and the second organic molecular film 7 on the surface of the nanoparticle 4. Thus, the film 5 can have a high density and can effectively cap surface defects, thereby contributing to surface passivation and decreasing energy loss. Consequently, the emission quantum yield is improved to 10% or more, preferably 30% or more, and the emission quantum yield is 2.5 times or more the emission quantum yield of the film 5 without the double structure.

Furthermore, due to hydrophilicity imparted to the film 5 by the ultrasonic irradiation, even when applied to a biological material labeling agent for bioimaging, the light-emitting body 3 can be suitable for bioimaging without adsorption of a nonpolar organic solvent harmful to cells on a biological constituent.

Thus, in the present embodiment, the film 5 formed by the ultrasonic irradiation and having the double structure improves the emission quantum yield to 10% or more, preferably 30% or more, and increases the emission quantum yield by 2.5 times or more the emission quantum yield before the ultrasonic irradiation. The upper limit of the emission quantum yield is typically, but not limited to, 50% or less.

It should be noted that the formation of a surface protective agent during the synthesis of nanoparticles, immediate addition of a fatty acid without an alkylthiol, and subsequent ultrasonic irradiation as in Non Patent Document 1 may impart hydrophilicity to the film but leave many uncapped surface defects, thus resulting in a low emission quantum yield.

To impart hydrophilicity, in addition to the ultrasonic irradiation, a thiol (—SH) or carboxy (—COOH) group with hydrophilicity may substitute for an organic ligand of a surface protective agent. Also in such a case, however, even if hydrophilicity can be imparted, the emission quantum yield is difficult to improve. More specifically, in such a case, during ligand substitution, atoms on the surface of nanoparticles may be removed together with the eliminated ligand and form a new surface defect, or a ligand to be substituted is not sufficiently present on the surface of nanoparticles, and the surface of the nanoparticles is highly reactive and cannot be sufficiently deactivated, so that it is not possible to improve the emission quantum yield and achieve desired luminous efficiency.

Thus, to improve the emission quantum yield to 10% or more, preferably 30% or more, it is important to emit ultrasonic waves during the formation of the second organic molecular film 6, form the film 5 with a double structure composed of the first organic molecular film 6 and the second organic molecular film 7, and sufficiently cap surface defects to reduce energy loss.

Next, the light-emitting body 3 according to an embodiment of the present invention is described in more detail.

Figure 3:
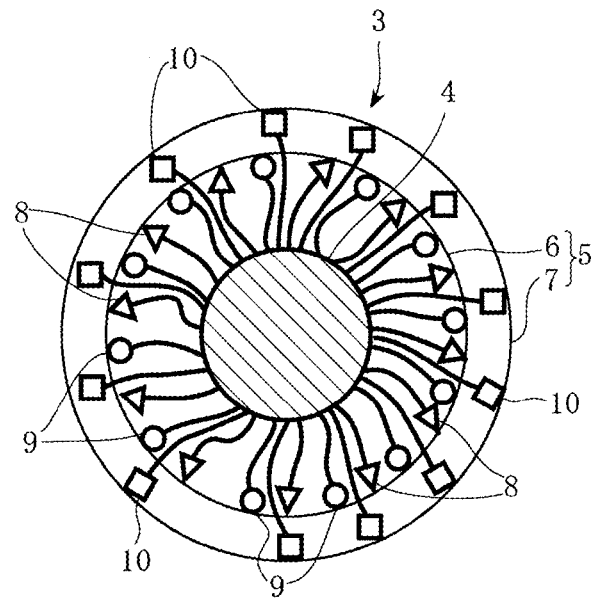
FIG. 3 is a schematic view of one embodiment (a first embodiment) of the light-emitting body.

FIG. 3 is a schematic enlarged view of the light-emitting body 3, wherein a surface protective agent 8 composed of an organic ligand is formed on the surface of the nanoparticle 4, as described above. Thus, the nanoparticle 4 has many surface defects on its surface, as described above, has high reactivity, and aggregates easily together with other nanoparticles 4. Thus, when the nanoparticle 4 is synthesized, the surface protective agent 8 acting as an organic ligand is usually coordinated to the surface of the nanoparticle 4 to partly cap surface defects, remove the surface defects, and promote passivation.

More specifically, the surface protective agent 8 is composed of an organic ligand with a hydrophobic group, such as an alkyl group (—$CH_2$), and a hydrophilic group, such as a thiol group (—SH), a carboxy group (—COOH), or an amino group (—$NH_2$). The hydrophilic group adsorbs on the surface of the nanoparticle 4, and the hydrophobic group is coordinated to be positioned on the outside.

In the surface protective agent 8, a solvent used in the synthesis of the nanoparticle 4 is formed as an organic ligand on the surface of the nanoparticle 4 after the synthesis. Thus, the surface protective agent 8 may be a high-boiling-point chemically stable solvent that prevents aggregation of nanoparticles 4 and contributes to surface passivation.

Examples of the surface protective agent 8 include alkylthiols, such as n-octyl thioglycolate ($CH_3(CH_2)_7OC(=O)CH_2SH$), 1-dodecanethiol ($CH_3(CH_2)_{11}SH$), and n-hexanethiol ($CH_3(CH_2)_5SH$), alkylamines, such as oleylamine ($H_2N(CH_2)_8HC=CH(CH_2)_7CH_3$), and n-octyl ether ($H_3C(CH_2)_7O(CH_2)_7CH_3$). In particular, the coordination power of the surface protective agent 8 has an influence on the particle size of the nanoparticle 4, and therefore the surface protective agent 8 is preferably selected in accordance with the required particle size. For example, for light emission at a shorter wavelength in the near-infrared region, it is preferable to use a combination of n-octyl thioglycolate and oleylamine, which provides an average particle size of approximately 5 nm. For light emission at a longer wavelength, it is preferable to use a combination of 1-dodecanethiol and oleylamine, which provides an average particle size in the range of approximately 6 to 7 nm.

An alkylthiol 9 (general formula $CH_3(CH_2)_nSH$) is adsorbed on the surface of the nanoparticle 4 between molecules of the surface protective agent 8. More specifically, the surface defects of the nanoparticle 4 cannot be sufficiently removed only by the surface protective agent 8, and in the present embodiment surface defects between molecules of the surface protective agent 8 are further removed by capping with the alkylthiol 9.

More specifically, the thiol group (—SH) of the alkylthiol 9, which is a hydrophilic group, adsorbs on surface defects of the nanoparticle 4 between molecules of the surface protective agent 8, and the alkyl group (—$CH_2$), which is a hydrophobic group, is coordinated to be positioned on the outside. The surface protective agent 8 composed of an organic ligand and the alkylthiol 9 coordinated between molecules of the surface protective agent 8 form the first organic molecular film 6 and effectively cap the surface defects.

Furthermore, the second organic molecular film 7 composed mainly of a fatty acid 10 (general formula $C_nH_mCOOH$) with a plurality of alkyl groups is formed on the surface of the nanoparticle 4 so as to form the double structure together with the first organic molecular film 6. The first and second organic molecular films 6 and 7 constitute the film 5. Thus, the alkyl group (—$CH_2$) of the fatty acid 10, which is a hydrophobic group, is adsorbed on the surface of the nanoparticle 4 between the first organic molecular films 6 by hydrophobic interaction described later, and the terminal carboxy group (—COOH), which is a hydrophilic group, is coordinated to be located at a terminal portion. Thus, in the film 5, the first organic molecular film 5 and the second organic molecular film 6 constitute the double structure on the nanoparticle 4 and form the high-density film 5, which contributes to surface passivation and more effectively removes surface defects. Furthermore, the ultrasonic irradiation places the carboxy group of the fatty acid 10 at a terminal portion and imparts hydrophilicity to the film 5, and therefore the light-emitting body 3 can be dispersed in water.

The alkylthiol 9 may be, but is not limited to, n-octyl thioglycolate ($CH_3(CH_2)_7OC(=O)CH_2SH$), 1-dodecanethiol ($CH_3(CH_2)_{11}SH$), or n-hexanethiol ($CH_3(CH_2)_5SH$).

The fatty acid 10 may be any fatty acid with a plurality of alkyl groups and may be oleic acid ($CH_3(CH_2)_7HC=CH(CH_2)_7COOH$), lauric acid ($CH_3(CH_2)_{10}COOH$), or octanoic acid ($CH_3(CH_2)_6COOH$).

To improve the emission quantum yield, the fatty acid 10 preferably has an alkyl group with a longer chain length than the alkyl group of the alkylthiol 9. For example, when the alkylthiol 9 is 1-dodecanethiol with "12" alkyl groups, the fatty acid 10 is preferably oleic acid with "15" alkyl groups. When the alkylthiol 9 is n-octyl thioglycolate with "8" alkyl groups, the fatty acid 10 is preferably lauric acid with "11" alkyl groups or oleic acid with "15" alkyl groups.

Thus, the light-emitting body 3 contains the nanoparticle 4 composed of a AgInSe compound semiconductor, and the film 5 with hydrophilicity has an emission quantum yield of 10% or more. Thus, the light-emitting body 3 has high luminous efficiency without adsorption of a nonpolar organic solvent harmful to cells on a biological tissue and is suitable for bioimaging.

Furthermore, the light-emitting body 3 has an emission intensity peak wavelength in the range of 650 to 1000 nm and a half-width of 100 nm or less at the peak wavelength.

Thus, even when the surface of the nanoparticle 4 is made hydrophilic, the light-emitting body 3 can retain its emission spectral characteristics with a good half-width ΔH in the near-infrared region, have high resolution, have good emission spectral characteristics, and is suitable for bioimaging. The light-emitting body 3 can have both good emission spectral characteristics and high luminous efficiency.

In particular, the film 5 with the double structure having the first organic molecular film 6 containing at least the alkylthiol 9 and the second organic molecular film 7 composed mainly of the fatty acid 10 with a plurality of alkyl groups can have a high density, can effectively cap surface defects of the nanoparticle 4, and contributes to surface passivation. Unlike hydrophilicity imparted by a ligand substitution reaction, hydrophilicity is imparted to the film 5 by the ultrasonic irradiation, as described above. Thus, the film 5 can prevent the formation of a new surface defect. Thus, it is possible to provide a light-emitting body that has high luminous efficiency with an emission quantum yield of 10% or more, preferably 30% or more, has both hydrophilicity and high luminous efficiency, and is suitable for bioimaging.

Next, an embodiment of a method for producing a light-emitting body is described in detail with reference to FIGS. 4 to 9.

[Preparation of Nonpolar Nanoparticle Dispersion Liquid]

Figure 4A:
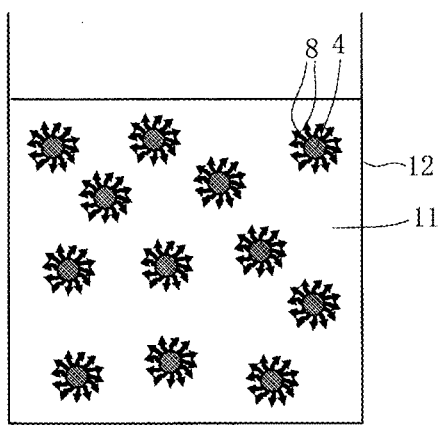
FIGS. 4(a) and 4(b) are process drawings (1/6) for explaining one embodiment of a method for producing a light-emitting body according to the present invention.
Figure 4B:
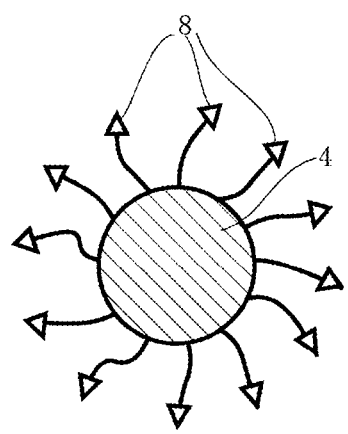

FIG. 4(a) illustrates a nonpolar nanoparticle dispersion liquid 12, in which the nanoparticles 4 with the surface protective agent 8 formed thereon are dispersed in a nonpolar solvent 11. FIG. 4(b) is a schematic enlarged view of details of the nanoparticle 4.

The nonpolar nanoparticle dispersion liquid 12 can be produced as described below.

First, a Ag compound containing a Ag component and an In compound containing an In component are prepared, and the Ag compound and the In compound are weighed such that the blend ratio of the In component to the Ag component, that is, the In/Ag ratio after synthesis preferably ranges from approximately 1.5 to 3 and is preferably higher than the stoichiometric composition. The In/Ag ratio can be adjusted in this manner to provide a sharp emission spectrum with a steep emission intensity peak wavelength and a small half-width ΔH.

The Ag compound and the In compound may be of any type and are preferably relatively inexpensive, chemically stable, and readily available metal complexes, for example, metal complexes having a fatty acid ion, such as an acetate ion, as a ligand, such as silver acetate ($Ag(OCOCH_3)$) and indium acetate ($In(OCOCH_3)_3$).

Next, these weighed materials are dissolved in a solvent to prepare a Ag—In solution. This solvent forms the surface protective agent 8 as an organic ligand after synthesis, as described above, and may be a mixed solution containing at least one selected from n-octyl thioglycolate, 1-dodecanethiol, oleylamine, and n-octyl ether described above.

Next, a Se powder is prepared, and the Se powder is dissolved in a solvent to prepare a Se solution. Also in this case, the solvent may be a mixed solution of an alkylthiol, such as 1-dodecanethiol or hexanethiol, and an alkylamine, such as oleylamine, as described above, or a phosphine, such as tributylphosphine or trioctylphosphine.

Next, the Ag—In solution is poured in a container, is vacuum degassed, is purged with nitrogen, and is then heat-treated to increase the reaction field temperature from room temperature to a predetermined temperature (for example, 100° C. to 150° C.).

Next, the Se solution is poured into the Ag—In solution heated to the predetermined temperature. The mixed solution is then further heated to a predetermined reaction temperature and is held at the reaction temperature (for example, 200° C. or more) for a predetermined reaction time (for example, 30 to 120 minutes). Thus, a reaction product is obtained.

The reaction product is then allowed to cool to room temperature and is then centrifuged to separate the supernatant from the precipitate. The supernatant is recovered, and the precipitate is discarded. Then, a poor solvent, such as methanol, ethanol, acetone, or acetonitrile, is added to the supernatant to form a precipitate. The precipitate is separated and recovered by centrifugation again. The operation of addition of a poor solvent→centrifugation→recovery of precipitate is then repeated multiple times to prepare a high-purity precipitate without impurities, such as a different phase, that is, the nanoparticle 4 of the AgInSe compound semiconductor covered with the surface protective agent 8. The nanoparticles 4 are then dispersed in a nonpolar solvent, such as chloroform, toluene, or hexane, to prepare the nonpolar nanoparticle dispersion liquid 12 as illustrated in FIG. 4(a).

[Preparation of Precursor Dispersion Liquid]

The alkylthiol 9 is added to the nonpolar nanoparticle dispersion liquid 12. As illustrated in FIG. 5(b), the alkylthiol 9 is coordinated such that the terminal thiol group, which is a hydrophilic group, is adsorbed on the surface of the nanoparticle 4 and the alkyl group, which is a hydrophobic group, is positioned on the outside. The alkylthiol 9 caps surface defects of the nanoparticle 4, and the surface protective agent 8 and the alkylthiol 9 form the first organic molecular film 6. As illustrated in FIG. 5(a), the nanoparticles 4 covered with the first organic molecular film 5 are dispersed in the nonpolar solvent 11. Thus, a precursor dispersion liquid 14 is prepared.

[Preparation of Fatty Acid Aqueous Solution]

As illustrated in FIG. 6, the fatty acid 10, such as oleic acid, is dissolved in an aqueous solution 15 to which an alkali, such as NaOH or KOH, is added to prepare a fatty acid aqueous solution 16.

[Preparation of Phase-Separated Solution]

Figure 7:
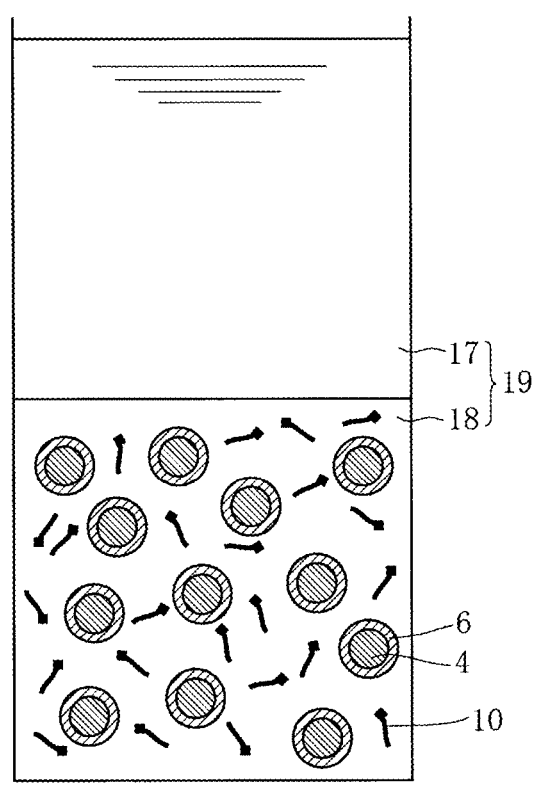
FIG. 7 is a process drawing (4/6) for explaining one embodiment of a method for producing a light-emitting body according to the present invention.

The fatty acid aqueous solution 16 is stirred to the extent that the whole foams, and is mixed with the precursor dispersion liquid 14. As illustrated in FIG. 7, the fatty acid 10 is dispersed in a nonpolar solvent phase 18, and a phase-separated solution 19 of an aqueous phase 17 and the nonpolar solvent phase 18 is prepared.

[Ultrasonic Irradiation]

Figure 8A:
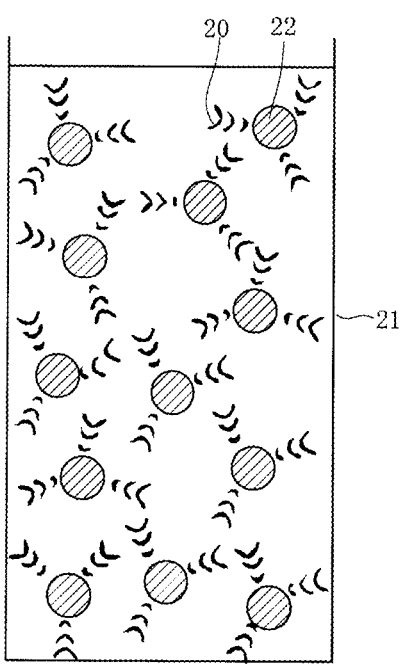
FIGS. 8(a) to 8(d) are process drawings (5/6) for explaining one embodiment of a method for producing a light-emitting body according to the present invention.
Figure 8B:
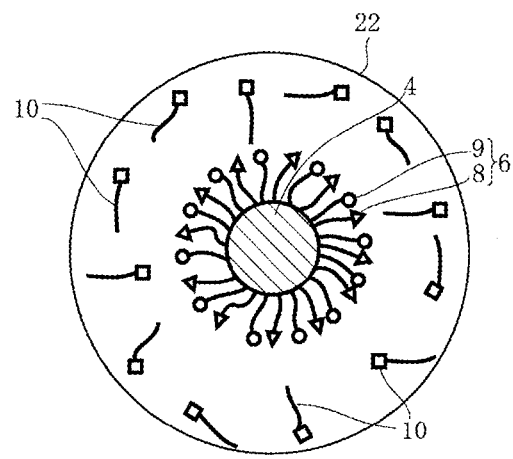

Ultrasonic waves 20 are applied to the phase-separated solution 19. This applies a large impact force to the phase-separated solution 19. As illustrated in FIG. 8(a), the aqueous phase 17 and the nonpolar solvent phase 18 are mixed to form a uniform aqueous solution 21, and an oil-in-water microemulsion 22 is formed in the aqueous solution 21. At this time, as illustrated in FIG. 8(b), the nanoparticle 4 with the first organic molecular film 6 formed thereon and the fatty acid 10 are confined in the microemulsion 22.

Figure 8C:
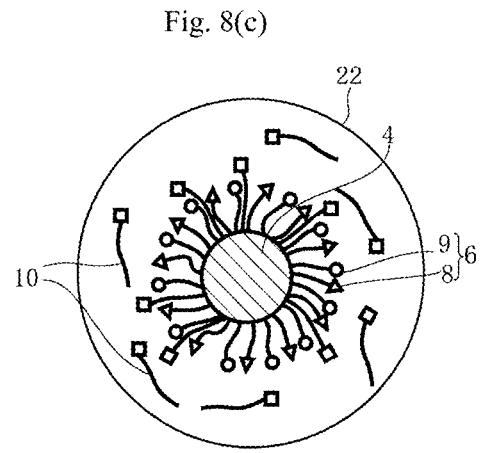
Figure 8D:
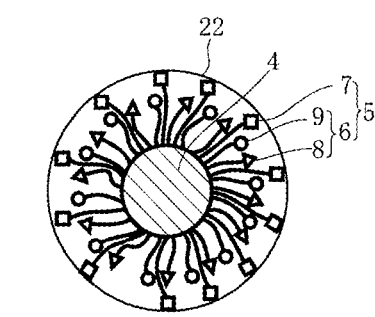

When the ultrasonic waves 20 are continuously applied to the aqueous solution 21, as illustrated in FIGS. 8(c) and 8(d), the microemulsion 22 gradually becomes smaller with the lapse of irradiation time, and the second organic molecular film 7 is formed on the surface of the nanoparticle 4 so as to form the double structure together with the first organic molecular film 6. More specifically, immediately after the microemulsion 22 is formed, the fatty acid 10 is suspended in the microemulsion 22, as illustrated in FIG. 8(b). When the ultrasonic waves 20 are continuously applied and a large impact force is applied to the microemulsion 22, the microemulsion 22 gradually becomes smaller. As the microemulsion 22 becomes smaller, part of the fatty acid 10 approaches the nanoparticle 4, and the alkyl group of the fatty acid 10 is adsorbed on the surface of the nanoparticle 4 by hydrophobic interaction caused by van der Waals force between the alkyl group of the fatty acid 10 and the alkyl group of the first organic molecular film 6, as illustrated in FIG. 8(c). Thus, the terminal carboxy group of the fatty acid 10 is positioned on the outside. When the ultrasonic waves 20 are further applied, as illustrated in FIG. 8(d), the microemulsion 22 becomes much smaller, the fatty acid 10 is progressively adsorbed on the nanoparticle 4 and is self-organized, and the fatty acid 10 becomes the second organic molecular film 7 and effectively caps surface defects between the first organic molecular films 6.

Thus, the fatty acid 10 is coordinated such that the alkyl group (—$CH_2$), which is a hydrophobic group, is adsorbed on the surface of the nanoparticle 4 and the terminal carboxy group (—COOH), which is a hydrophilic group, is positioned on the outside. The carboxy group imparts hydrophilicity to the film 5. Thus, the first organic molecular film 6 and the second organic molecular film 7 are densely coordinated on the surface of the nanoparticle 4 and form the film 5 with the double structure to which hydrophilicity is imparted.

[Preparation of Aqueous Nanoparticle Dispersion]

Figure 9:
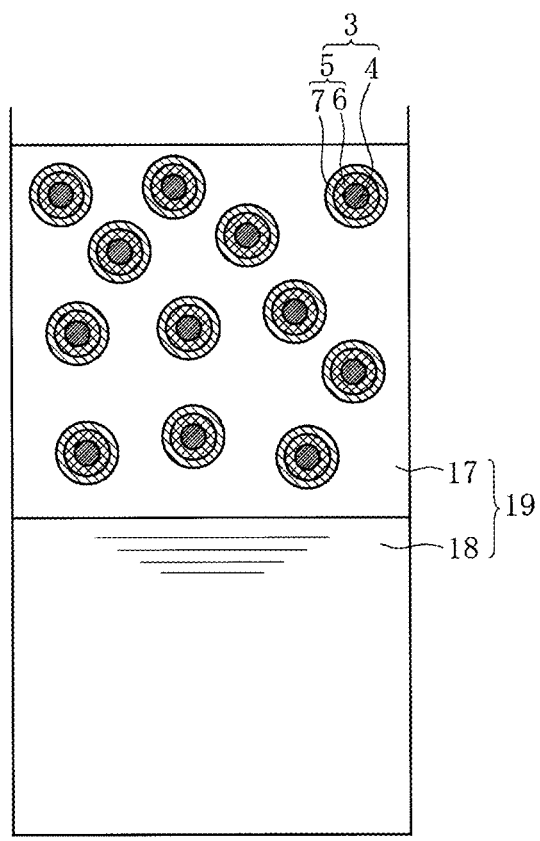
FIG. 9 is a process drawing (6/6) for explaining one embodiment of a method for producing a light-emitting body according to the present invention.

When the microemulsion 22 becomes sufficiently small, the ultrasonic irradiation is completed. Then, as illustrated in FIG. 9, the aqueous solution 21 is separated again into the aqueous phase 17 and the nonpolar solvent phase 18 and forms the phase-separated solution 19. The light-emitting body 3 having the film 5 with hydrophilicity moves to the aqueous phase 17 and is dispersed in the aqueous phase 17.

Subsequently, an appropriate amount of organic solvent, such as chloroform, is added, and centrifugation is repeated to recover the aqueous phase 17. An organic solvent, such as hexane, is added to the recovered aqueous phase 17, and centrifugation is repeated again to recover the aqueous phase 17. Thus, a high-purity aqueous nanoparticle dispersion containing nanoparticles dispersed in water can be prepared.

In such a method for producing a light-emitting body, first, the thiol group of the alkylthiol 9 is adsorbed on surface defects of the nanoparticle 4 and forms the first organic molecular film 6 on the surface of the nanoparticle 4, thereby producing the precursor dispersion liquid 14. Subsequently, the fatty acid aqueous solution 16 and the precursor dispersion liquid 14 are mixed to prepare the phase-separated solution 19, and the ultrasonic waves 20 are applied to the phase-separated solution 19 to form the microemulsion 22 and confine the nanoparticle 4 and the fatty acid 10 in the microemulsion 22. The alkyl group of the fatty acid 10 is adsorbed on the surface of the nanoparticle 4 by the hydrophobic interaction with the alkyl group of the alkylthiol 9, and the second organic molecular film 7 composed mainly of the fatty acid 10 is formed on the surface of the nanoparticle 4 so as to overlap the first organic molecular film 6. Thus, the film 5 with the double structure composed of the first organic molecular film 6 and the second organic molecular film 7 is formed on the surface of the nanoparticle 4. The terminal carboxy group of the fatty acid 10 imparts hydrophilicity to the film 5. Thus, in the phase-separated solution 19 that is phase-separated again after ultrasonic irradiation, the nanoparticle 4 having the film 5 with hydrophilicity moves to the aqueous phase 17 and is dispersed in water. Thus, the light-emitting body 3 with good emission spectral characteristics and high luminous efficiency suitable for a biological material labeling agent can be produced.

Second Embodiment

The nanoparticle 4 in the first embodiment is formed of the AgInSe compound semiconductor, whereas the nanoparticle 4 in a second embodiment is formed of a AgInGaSe compound semiconductor in which a Ga component is introduced into a AgInSe compound semiconductor.

The AgInGaSe compound semiconductor has slightly higher band-gap energy than the AgInSe compound semiconductor, has an absorption edge shifted to the short wavelength side, and can emit light at a shorter wavelength in the near-infrared region while maintaining a half-width ΔH of 100 nm or less. In particular, the blend ratio of Ga to In, that is, the Ga/In ratio can be changed to control the emission intensity peak wavelength without changing the average particle size.

The method for producing a light-emitting body according to the second embodiment is the same as in the above embodiment except that a Ga compound in addition to the Ag compound and the In compound is dissolved in a solvent to prepare a Ag—In—Ga solution.

The Ga compound may be, but is not limited to, gallium acetylacetonate represented by the chemical formula (1).

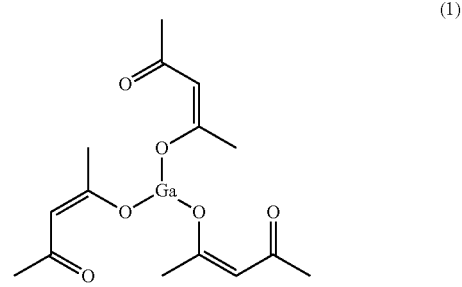

(1)

Third Embodiment

Figure 10:
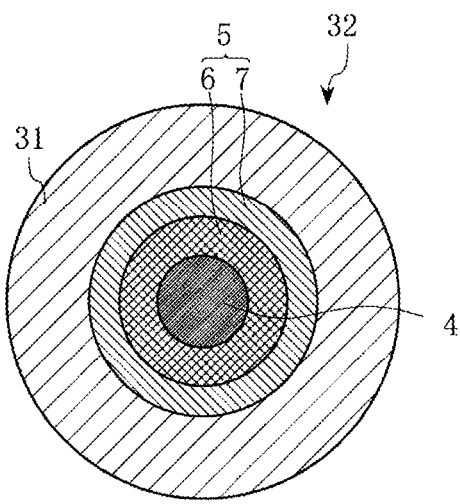
FIG. 10 is a schematic cross-sectional view of a second embodiment of a light-emitting body according to the present invention.

FIG. 10 is a schematic cross-sectional view of a third embodiment of a light-emitting body according to the present invention.

In the third embodiment, in addition to the first embodiment, the film 5 is covered with a surface modifier 31 composed mainly of a cationic cell-penetrating peptide.

The cationic cell-penetrating peptide is attracted to a negatively charged cell membrane on the surface of a biological material by electrostatic interaction, as described later, and a light-emitting body 32 can be easily introduced into the biological material by endocytosis. Thus, various types of biological information can be detected only by irradiating the light-emitting body 32 with light.

Furthermore, unlike Cd compound semiconductors, a AgInSe compound semiconductor serving as a light source of the light-emitting body 32 has low toxicity. Thus, even a larger amount of the light-emitting body introduced into a biological material causes less cell death and can successfully maintain the cell survival rate. Incidentally, as described later, when the present inventors added the light-emitting body 32 at different molar concentrations to a cell culture fluid of adipose-derived stem cells (ASCs), it has been confirmed that the light-emitting body 32 introduced into a cell even at 160 nmol/L on a molar concentration basis can have a cell survival rate of 80% or more.

The cell-penetrating peptide may be any cell-penetrating peptide that is cationic and promotes endocytosis, and is preferably octaarginine (R8: RRRRRRRR), which has eight arginine (R) moieties represented by the chemical formula (2) in its molecule.

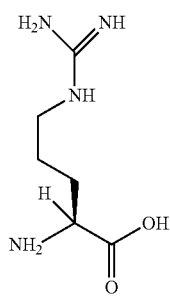

(2)

The light-emitting body according to the third embodiment can be produced as described below.

Figure 11:
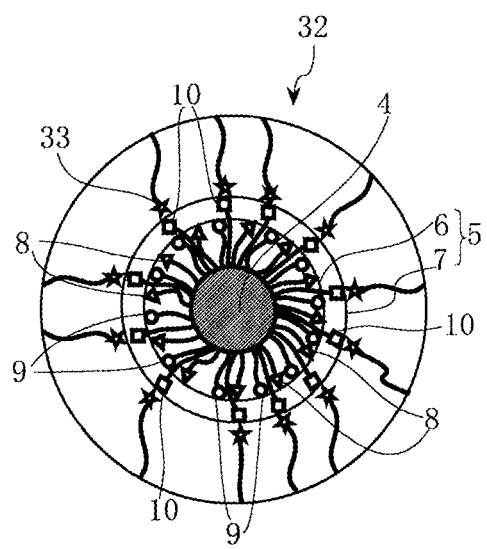
FIG. 11 is a schematic view of a principal part of a production process according to the second embodiment.

FIG. 11 is a schematic view of a principal part of a process of producing the light-emitting body.

First, the nanoparticle 4 covered with the film 5 is formed by the same method and procedure as in the first embodiment.

More specifically, the nanoparticle 4 is formed of a AgInSe compound semiconductor, and the film 5 composed of the first organic molecular film 6 and the second organic molecular film 7 is formed on the surface of the nanoparticle 4. The first organic molecular film 6 has a hydrophilic group, such as a thiol group, adsorbed on the surface of the nanoparticle 4, and a hydrophobic group, such as an alkyl group, positioned on the outside. The second organic molecular film 7 is formed of the fatty acid 10. The alkyl group of the fatty acid 10 is adsorbed on the surface of the nanoparticle 4 between the first organic molecular films 6 by hydrophobic interaction, and the terminal carboxy group is positioned on the outside, thereby imparting hydrophilicity.

Next, the nanoparticle 4 with the film 5 formed thereon is mixed with the surface modifier 31 composed mainly of a cationic cell-penetrating peptide, such as R8. More specifically, the nanoparticle 4 and the surface modifier 31 are mixed in a liquid phase such that the mixing ratio of the cell-penetrating peptide to the nanoparticle 4 is sufficiently excessive, for example, approximately 10,000 in terms of a mole ratio. Thus, the surface of the second organic molecular film 7 is covered with the surface modifier 31. Thus, the light-emitting body 32 is formed. For example, when R8 is used as a cationic cell-penetrating peptide, the nanoparticle 4 with the film 5 formed thereon can be mixed with a large amount of R8 to allow the carboxy group (—COOH) of the second organic molecular film 7 in the film 5 to react with the guanidino group (—NH—(C=NH)—NH$_2$) of R8 and form a peptide bond (—NHCO—). Thus, the second organic molecular film 7 is bonded to R8, and the film 5 is covered with R8. Thus, the light-emitting body 32 surface-modified with R8 can be produced. Also in this case, the terminal carboxy group of R8 is in contact with the outside and can impart hydrophilicity.

<Biological Material Labeling Agent>

The light-emitting body 3 or 32 has hydrophilicity and has good emission spectral characteristics and high luminous efficiency. Thus, even when the light-emitting body 3 or 32 is introduced into a biological material, a biological image can be dynamically and efficiently analyzed with desired high sensitivity, with multiple colors, and without adsorption of a harmful substance, such as an organic solvent, on a biological tissue. Furthermore, without harmful elements, such as Cd, a biological material labeling agent with low toxicity suitable for a biomarker for bioimaging can be produced.

Figure 12:
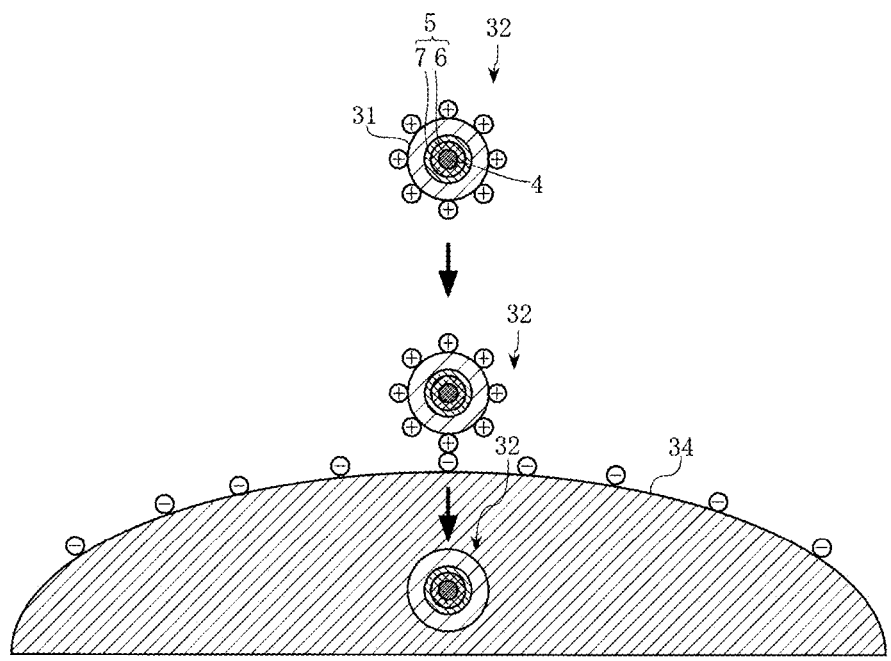
FIG. 12 is a view of a process of introducing a light-emitting body according to the present invention into a biological material.

FIG. 12 is a schematic view of a process of introducing a light-emitting body into a biological material. The light-emitting body is the light-emitting body according to the third embodiment.

The surface modifier 31 covering the film 5 is cationic and has a positive charge on its surface. Thus, due to electrostatic interaction between the surface modifier 31 and a negatively charged cell membrane 34 on the surface of the biological material, the surface modifier 31 is attracted to the surface of the cell membrane 34, and the light-emitting body 32 moves onto the cell membrane 34, as illustrated in FIG. 12. Subsequently, the light-emitting body 32 is transported and incorporated into the cell membrane 34 by endocytosis. Thus, the light-emitting body 32 fluoresces only by light irradiation and can be utilized as a biological material labeling agent.

Although the light-emitting body 32 is covered with the surface modifier 31 in the above embodiment, even the light-emitting body 3 not covered with a surface modifier, such as the light-emitting body 3 according to the first or second embodiment, can be introduced into a cell by endocytosis. In such a case, the second organic molecular film 7 on the surface of the light-emitting body 3 binds to a receptor on the cell membrane, and the light-emitting body 3 can be incorporated via the receptor into a biological material by endocytosis and can be utilized as a biological material labeling agent.

As described above, the light-emitting body 3 or 32 has hydrophilicity and has good emission spectral characteristics and high luminous efficiency. Thus, the state of a biological material can be examined only by irradiating the light-emitting body introduced into a living body with light, without adsorption of a harmful substance, such as an organic solvent, on the biological tissue. Thus, a biological image can be dynamically and efficiently analyzed with desired high sensitivity and with multiple colors, and a biological material labeling agent suitable for a biomarker for bioimaging can be produced.

It should be noted that the present invention is not limited to the above embodiments. It goes without saying that the above embodiments are embodiments of the present invention and can be modified without departing from the gist of the present invention. For example, although the AgInSe compound semiconductor is used as nanoparticles in the third embodiment, the AgInGaSe compound semiconductor as described in the second embodiment can, of course, also be used.

A light-emitting body according to the present invention can be used as a biological material labeling agent, as described above, and can also be utilized as a light source for exciting a label in a living body. For example, a light-emitting body according to the present invention filled in a seal portion of a blue light-emitting diode or an ultraviolet light-emitting diode is excited by the blue light-emitting diode or the ultraviolet light-emitting diode and emits light in the near-infrared region in the range of 650 to 1000 nm, and therefore can be utilized as light for exciting a label in a living body in such a wavelength range.

Next, examples of the present invention are specifically described.

Example 1

[Preparation of Sample]
<Preparation of Nonpolar Nanoparticle Dispersion Liquid>

A 99.99% pure Se powder (manufactured by Sigma-Aldrich Corporation), 99% pure silver acetate (manufactured by Nacalai Tesque, Inc.), and 99.99% pure indium acetate (manufactured by Alfa Aesar) were prepared as nanoparticle materials. 95% pure n-octyl thioglycolate (manufactured by Tokyo Chemical Industry Co., Ltd.), 80% pure oleylamine (manufactured by Acros Organics), and 95% pure n-octyl ether (manufactured by Tokyo Chemical Industry Co., Ltd.) were prepared as solvents.

Then, 0.133 mmol of silver acetate and 0.267 mmol of indium acetate were weighed such that the Ag/In ratio after synthesis was ½. The weighed materials and a stirrer tip were put into a 50-mL three-neck flask. Then, 1 mL of n-octyl thioglycolate and 9 mL of n-octyl ether were added and stirred to prepare a Ag—In solution.

Furthermore, 0.4 mmol of a Se powder was dissolved in 1 mL of n-octyl thioglycolate and 1 mL of oleylamine and was heated to 80° C. to prepare a Se solution.

Next, the three-neck flask containing the Ag—In solution was vacuum degassed, was purged with nitrogen, and was heated with a heater from room temperature to 100° C. When the temperature of the reaction field reached 100° C., the Se solution was injected into the three-neck flask, the temperature of the reaction field was increased to 200° C., and heat treatment was performed at this temperature for 60 minutes to produce a reaction product.

The reaction product was then air-cooled to room temperature and was centrifuged at a rotational speed of 5000 rpm for 5 minutes to separate into a supernatant and a precipitate. The supernatant was recovered, and the precipitate was discarded.

Then, ethanol (purity: 99.5%, manufactured by Kanto Chemical Co., Inc.) in an amount approximately three times the volume of the supernatant was added to precipitate AgInSe nanoparticles. Centrifugation was then performed again to recover the nanoparticles, and 5 mL of ethanol was added to the recovered nanoparticles. The precipitated nanoparticles were dispersed with a vortex mixer and were centrifuged at a rotational speed of 5000 rpm for 5 minutes to recover crystal grains again. The operation of methanol addition→centrifugation→recovery of nanoparticles was then repeated multiple times. High-purity nanoparticles thus recovered were dispersed in a nonpolar solvent chloroform (purity: 99%, manufactured by Nacalai Tesque, Inc.) to prepare a nonpolar nanoparticle dispersion liquid. The nanoparticles dispersed in the nonpolar solution before ultrasonication were designated as a sample No. 11.

<Preparation of Precursor Dispersion Liquid to Phase-Separated Solution>

95% pure 1-dodecanethiol (manufactured by Tokyo Chemical Industry Co., Ltd.) was prepared as an alkylthiol, and 90% pure oleic acid (manufactured by Sigma-Aldrich Corporation) was prepared as a fatty acid.

The nonpolar nanoparticle dispersion liquid was adjusted to have an absorbance of 10 at a wavelength of 400 nm. Then, 16 mg of 1-dodecanethiol was added to 1 mL of the nonpolar nanoparticle dispersion liquid to cap surface defects of the nanoparticles, thereby forming a first organic molecular film. The nanoparticles with the first organic molecular film formed thereon were dispersed in the nonpolar solution to prepare a precursor dispersion liquid.

Next, 20 mL of pure water and 25 µL of 1M sodium hydroxide (purity: 97%, manufactured by Nacalai Tesque, Inc.) were added to a 50-mL beaker to prepare an alkaline aqueous solution, and 40 µL of oleic acid was added to the alkaline aqueous solution. The alkaline aqueous solution was stirred vigorously for 5 minutes to the extent that the whole foams, thereby preparing a fatty acid aqueous solution.

Subsequently, the precursor dispersion liquid and the fatty acid aqueous solution were mixed together to prepare a phase-separated solution of a chloroform phase and an aqueous phase.

<Ultrasonic Irradiation>

Ultrasonic waves were applied to the phase-separated solution with an ultrasonic homogenizer (UX-300, manufactured by Mitsui Electric Co., Ltd.).

This ultrasonic homogenizer is composed of an oscillator and a vibrator, and the output from the oscillator is converted into vibrational energy by the vibrator. A tip of the vibrator vibrates vertically, and a strong shock wave is applied to the phase-separated solution. Thus, the strong shock wave caused by ultrasonic irradiation forms a uniform aqueous solution and can form an oil-in-water microemulsion in the aqueous solution.

The tip had a diameter of 12φ. While a probe was immersed approximately 1 cm in the phase-separated solution, ultrasonic waves were continuously applied for 30 minutes. The output of the ultrasonic homogenizer was set such that an output display bar graph (output power) on an operation screen of the ultrasonic homogenizer exhibited approximately 50%.

<Preparation of Aqueous Nanoparticle Dispersion>

When the ultrasonic irradiation was completed, the aqueous solution was phase-separated again into an aqueous phase and a chloroform phase, and nanoparticles with hydrophilicity moved to the aqueous phase.

Next, 10 mL of chloroform was added to the aqueous phase and was stirred. Centrifugation was then performed at a rotational speed of 5000 rpm for 2 minutes. A series of operations for recovering the aqueous phase were performed twice. Next, 10 mL of 96% pure hexane (manufactured by Nacalai Tesque, Inc.) was added to the recovered aqueous phase and was stirred. The aqueous phase was then washed twice by centrifugation at a rotational speed of 5000 rpm for 2 minutes. Thus, a high-purity aqueous nanoparticle dispersion was produced. The nanoparticles dispersed in the aqueous solution after ultrasonication were designated as a sample No. 12.

[Sample Evaluation]

FIG. 13 shows the phase-separated solution before and after ultrasonic irradiation.

Figures 13A, 13B:
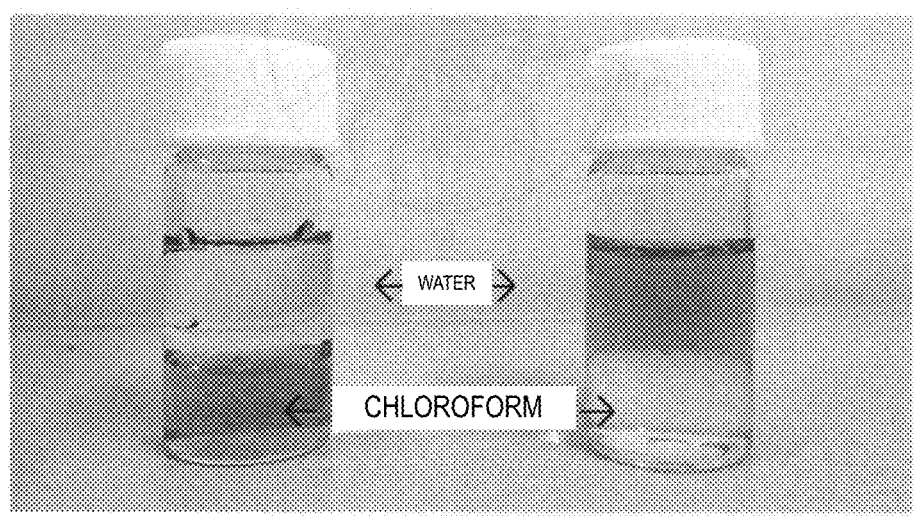
FIGS. 13(a) and 13(b) are photographs of a phase-separated solution before and after ultrasonic irradiation in Example 1.

FIG. 13(a) is before the ultrasonic irradiation, and FIG. 13(b) is after the ultrasonic irradiation. The solution is phase-separated into an aqueous phase and a chloroform phase both before and after the ultrasonic irradiation. The nanoparticles serving as the core of the light-emitting body are dispersed in the nonpolar solvent chloroform phase before the ultrasonic irradiation, as illustrated in FIG. 13(a), and are dispersed in the aqueous phase after the ultrasonication, as illustrated in FIG. 13(b). Thus, it was confirmed that the nanoparticles in the chloroform phase before the ultrasonic irradiation moved to the aqueous phase after the ultrasonic irradiation, and hydrophilicity was imparted to the light-emitting body.

Next, an absorption spectrum and a transmission spectrum of the sample No. 12 after the ultrasonication were measured with an ultraviolet visible near-infrared spectrophotometer (manufactured by Hitachi High-Technologies Corporation, U4100) under the measurement conditions of an optical path length of 1 cm and a measurement wavelength range of 300 to 1500 nm.

Figure 14:
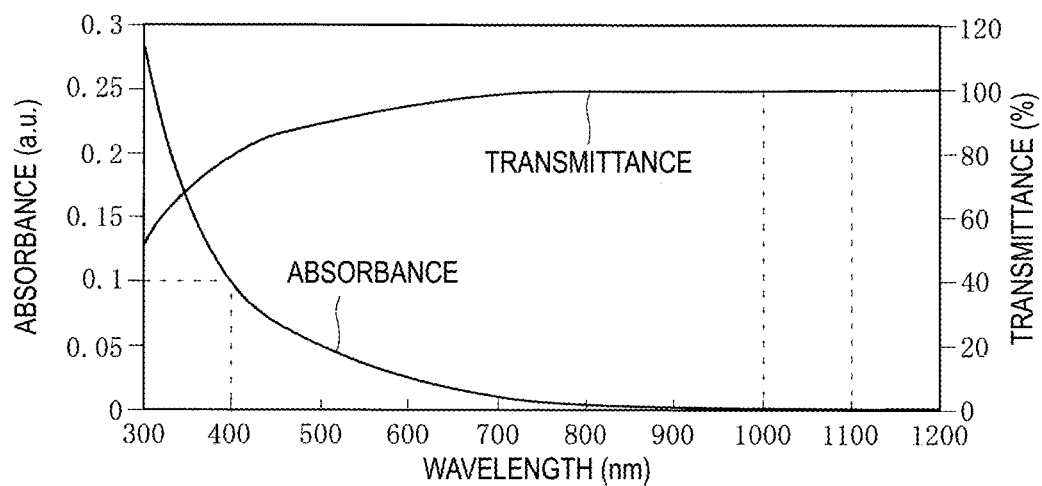
FIG. 14 is a profile of each of an absorption spectrum and a transmission spectrum in Example 1.

FIG. 14 shows an absorption spectrum and a transmission spectrum of the sample No. 12 when the absorbance at a wavelength of 400 nm is normalized to be 0.1. In the figure, the horizontal axis represents the wavelength (nm), the left vertical axis represents the absorbance (a.u.), and the right vertical axis represents the transmittance (%). In FIG. 14, absorption of the solvents chloroform and water before and after the ultrasonic irradiation is removed.

As is clear from FIG. 14, the transmittance was almost 100% in the wavelength range of 1000 to 1100 nm, indicating that the light-emitting body was accurately dispersed in water.

Next, the emission quantum yields and emission spectra of the sample No. 11 and the sample No. 12 were measured with an absolute emission quantum yield measuring apparatus (C9920-02 manufactured by Hamamatsu Photonics K.K.) at a room temperature of 25° C.

As a result, the sample No. 11 (before the ultrasonic irradiation) had an emission quantum yield of 9%, but the sample No. 12 (after the ultrasonic irradiation) had an emission quantum yield of 44%. Thus, it was found that the emission quantum yield after the ultrasonic irradiation was 4.9 times the emission quantum yield before the ultrasonic irradiation and was significantly improved.

Figure 15:
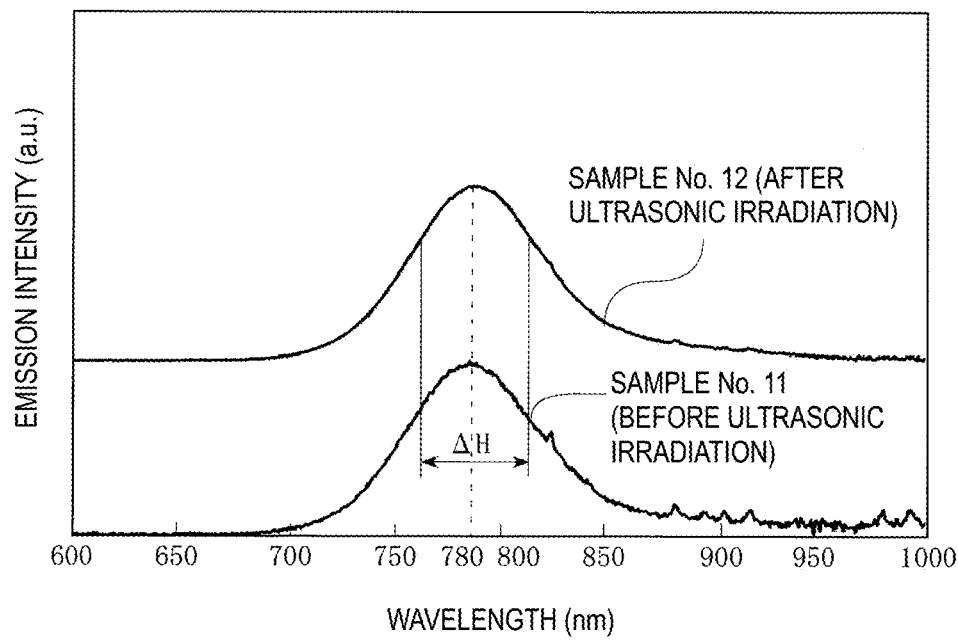
FIG. 15 is a profile of each emission spectrum of a sample No. 11 (before ultrasonic irradiation) and a sample No. 12 (after the ultrasonic irradiation) in Example 1.

FIG. 15 shows emission spectra of the sample No. 11 and the sample No. 12. In the figure, the horizontal axis represents the wavelength (nm), and the vertical axis represents the emission intensity (a.u.).

As is clear from FIG. 15, both the sample No. 11 and the sample No. 12 had an emission intensity peak wavelength of 780 nm and a half-width ΔH of 70 nm, indicating that the ultrasonic irradiation did not affect the emission spectral characteristics.

Figure 16:
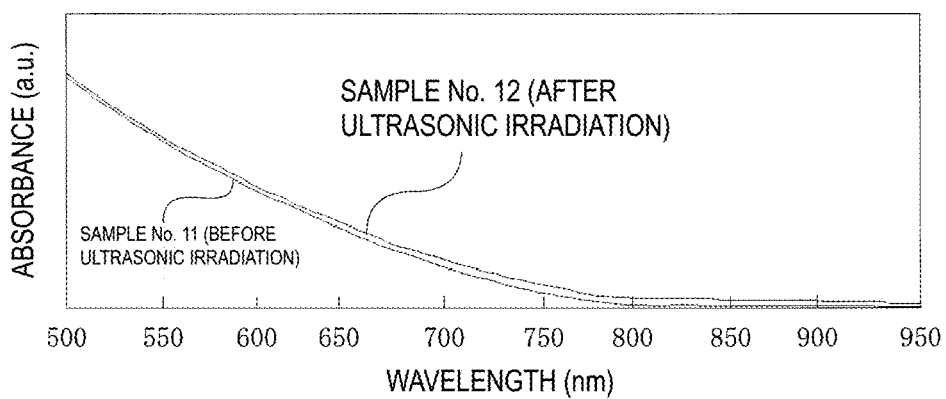
FIG. 16 is a profile of each absorption spectrum of the sample No. 11 (before ultrasonic irradiation) and the sample No. 12 (after the ultrasonic irradiation) in Example 1.

FIG. 16 is a profile of an absorption spectrum of the sample No. 11 (before the ultrasonic irradiation) in comparison with the absorption spectrum of the sample No. 12 (after the ultrasonic irradiation) (FIG. 14). In the figure, the horizontal axis represents the wavelength (nm), and the vertical axis represents the absorbance (a.u.).

As is clear from FIG. 16, there was almost no change in the absorption edge wavelength before and after the ultrasonic irradiation, and it was found that the ultrasonic irradiation did not affect the band-gap energy of the nanoparticles.

Next, STEM images of the sample No. 11 and the sample No. 12 were taken with a scanning transmission electron microscope (hereinafter referred to as "STEM") (manufactured by Hitachi High-Technologies Corporation, HD-2300A) at a magnification of 600 k.

Figure 17A:
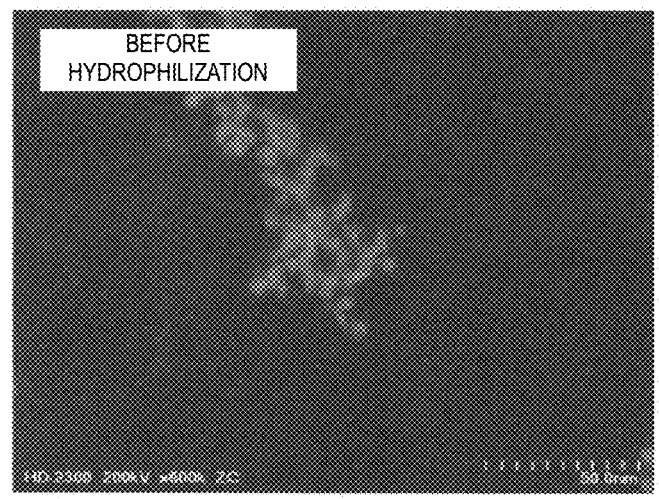
FIGS. 17(a) and 17(b) are STEM images of each of the sample No. 11 (before hydrophilization) and the sample No. 12 (after the hydrophilization) in Example 1.
Figure 17B:
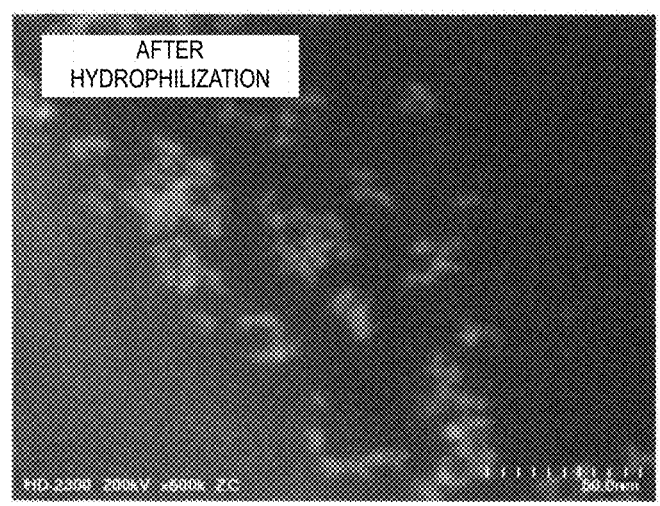

FIG. 17 shows images thus taken.

As is clear from FIG. 17, the nanoparticles had an average particle size of approximately 5 nm before and after the ultrasonic irradiation (before and after the hydrophilization), and it was confirmed that there was no change in shape or size.

Thus, it was found that applying ultrasonic waves to the nanoparticles for hydrophilization can significantly improve the emission quantum yield while maintaining the emission intensity peak wavelength, the half-width ΔH, and the average particle size.

Example 2

Preparation of Samples of Examples

1-Dodecanethiol (purity: 95%, manufactured by Tokyo Chemical Industry Co., Ltd.) was used instead of n-octyl thioglycolate to prepare a nonpolar nanoparticle dispersion liquid.

More specifically, 0.067 mmol of silver acetate and 0.134 mmol of indium acetate were weighed such that the Ag/In ratio after synthesis was ½. The weighed materials and a stirrer tip were put into a 50-mL three-neck flask. Then, 1 mL of 1-dodecanethiol and 8 mL of n-octyl ether were added and stirred to prepare a Ag—In solution.

0.2 mmol of a Se powder was dissolved in 1 mL of 1-dodecanethiol and 1 mL of oleylamine and was heated to 80° C. to prepare a Se solution.

Next, the three-neck flask containing the Ag—In solution was vacuum degassed, was purged with nitrogen, and was heated with a heater from room temperature to 150° C.

When the temperature of the reaction field reached 150° C., the Se solution was injected into the three-neck flask, the temperature of the reaction field was increased to 200° C., and heat treatment was performed at this temperature for 120 minutes to produce a reaction product.

The reaction product was then air-cooled to room temperature and was centrifuged at a rotational speed of 5000 rpm for 5 minutes to separate into a supernatant and a precipitate. The supernatant was recovered, and the precipitate was discarded.

Then, ethanol in an amount approximately three times the volume of the supernatant was added to precipitate AgInSe nanoparticles. Centrifugation was then performed again to recover the nanoparticles, and 5 mL of ethanol was added to the recovered nanoparticles. The precipitated nanoparticles were dispersed with a vortex mixer and were centrifuged at a rotational speed of 5000 rpm for 5 minutes to recover nanoparticles again. The operation of ethanol addition-→centrifugation→recovery of nanoparticles was then repeated multiple times. High-purity nanoparticles thus recovered were dispersed in chloroform to prepare a nonpolar nanoparticle dispersion liquid. The nanoparticles dispersed in the nonpolar solvent before the ultrasonic irradiation were designated as a sample No. 21.

Subsequently, an aqueous nanoparticle dispersion was prepared by the same method and procedure as in Example 1. The nanoparticles dispersed in the aqueous solution after the ultrasonication were designated as a sample No. 22.

[Preparation of Samples of Comparative Examples]

A nonpolar nanoparticle dispersion liquid was prepared by the same method and procedure as in the samples of the examples.

Next, 4 mL of 3-mercaptopropionic acid ($HS(CH_2)_2COOH$) (purity: 98%, manufactured by Nacalai Tesque, Inc.) was mixed with 15 mL of 2M potassium hydroxide (KOH) (purity: 85%, manufactured by Nacalai Tesque, Inc.). Then, 0.5 mL of the solution thus prepared and 1 mL of ethanol were put into a test tube.

The nonpolar nanoparticle dispersion liquid was then adjusted to have an absorbance of 1 at a wavelength of 400 nm, 1 mL of the nonpolar nanoparticle dispersion liquid was added to the test tube, and the tube was capped. The nonpolar nanoparticle dispersion liquid was then stirred overnight in a hot stirrer adjusted to a temperature of 60° C. to cause a ligand substitution reaction between 3-mercaptopropionic acid, 1-dodecanethiol, and oleylamine, thereby imparting hydrophilicity to the surface of the nanoparticles.

After air cooling, centrifugation was performed at 5000 rpm for 5 minutes to recover nanoparticles as precipitates. 5 mL of ethanol was added to the nanoparticles. The nanoparticles were dispersed with a vortex mixer and were washed by centrifugation again at 5000 rpm for 5 minutes. The nanoparticles recovered were dispersed in pure water and were then centrifuged at 5000 rpm for 5 minutes. The supernatant was recovered to prepare an aqueous nanoparticle dispersion. The nanoparticles dispersed in this aqueous solution were designated as a sample No. 23.

[Sample Evaluation]

An emission spectrum and emission quantum yield of each of the sample No. 21 to the sample No. 23 were measured by the same method and procedure as in Example 1.

Figure 18:
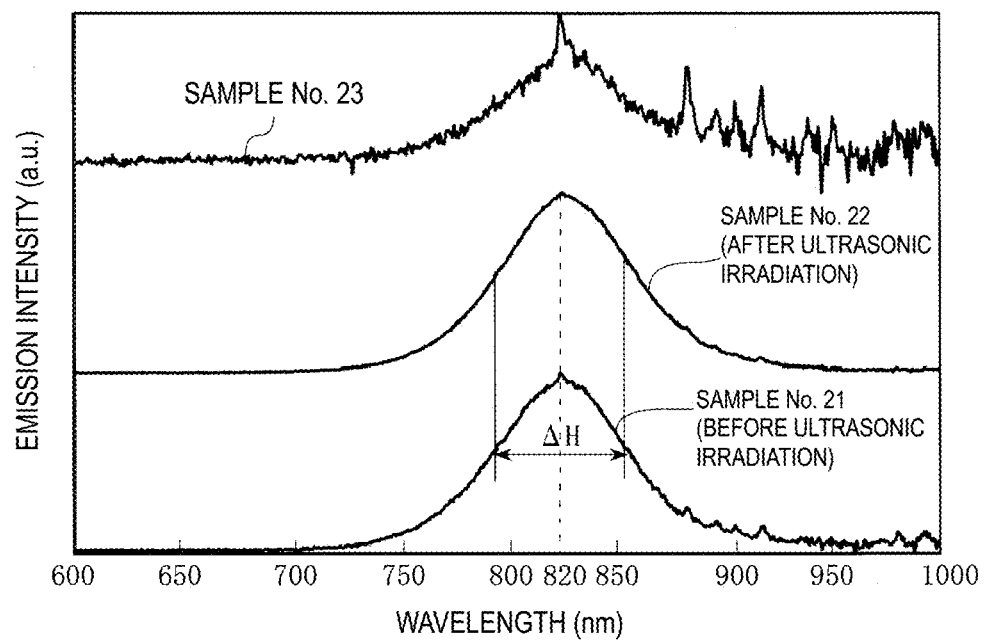
FIG. 18 is a profile of each emission spectrum of a sample No. 21 and a sample No. 22 before and after ultrasonic irradiation in Example 2.

FIG. 18 shows emission spectra of the sample No. 21 to the sample No. 23. In the figure, the horizontal axis represents the wavelength (nm), and the vertical axis represents the emission intensity (a.u).

Table 1 shows the emission intensity peak wavelength (nm), half-width ΔH, and emission quantum yield (%) of each of the sample No. 21 to the sample No. 23.

TABLE 1

| Sample No. | Peak wavelength (nm) | Half-width ΔH (nm) | Emission quantum yield (%) |
|---|---|---|---|
| 21* | 820 | 70 | 12 |
| 22 | 820 | 70 | 38 |
| 23* | — | — | 3 |

*Outside the scope of the present invention

As is clear from Table 1 and FIG. 18, in the sample 23, the emission spectrum was a very gentle curve, and an accurate half-width ΔH could not be measured. The emission quantum yield was as low as 3%.

The sample No. 21 had a peak wavelength of 820 nm, a half-width ΔH of 70 nm, which is 100 nm or less, good steepness and sharpness, but a low emission quantum yield of 12%.

In contrast, the peak wavelength and half-width ΔH of the sample No. 22 were the same as those of the sample No. 21 and did not change before and after the ultrasonic irradiation, but the sample No. 22 had an emission quantum yield of 38%, which was at least three times the emission quantum yield before the ultrasonic irradiation.

Thus, although hydrophilicity imparted by ligand substitution as in the sample No. 23 could not improve the emission quantum yield, ultrasonic irradiation as in the sample No. 22 could improve the emission quantum yield while maintaining the emission intensity peak wavelength and half-width ΔH. Thus, it was confirmed that ultrasonic irradiation was important to improve the emission quantum yield.

Example 3

99.99% pure gallium acetylacetonate (manufactured by Strem Chemicals) was prepared. Ga was injected into AgInSe to prepare AgInGaSe nanoparticles with different Ga contents. Emission spectra and emission quantum yields were evaluated.

0.133 mmol of silver acetate and 0.267 mmol of indium acetate were weighed, and gallium acetylacetonate was also weighed such that the Ga/In ratio was 0, 1, or 2. The weighed materials and a stirrer tip were put into a 50-mL three-neck flask. Then, 2 mL of n-octyl thioglycolate and 9 mL of n-octyl ether were added and stirred to prepare a AgInGa solution.

0.4 mmol of a Se powder was dissolved in 2 mL of n-octyl thioglycolate and 2 mL of oleylamine and was heated to 80° C. to prepare a Se solution.

Next, the three-neck flask containing the AgInGa solution was vacuum degassed, was purged with nitrogen, and was heated with a heater from room temperature to 100° C. When the temperature of the reaction field reached 100° C., the Se solution was injected into the three-neck flask, the temperature of the reaction field was increased to 200° C., and heat treatment was performed at this temperature for 60 minutes to produce a reaction product.

The reaction product was then air-cooled to room temperature and was centrifuged at a rotational speed of 5000 rpm for 5 minutes to separate into a supernatant and a precipitate. The supernatant was recovered, and the precipitate was discarded.

Then, ethanol in an amount approximately three times the volume of the supernatant was added to precipitate AgInGaSe nanoparticles. Centrifugation was then performed again to recover the nanoparticles, and 5 mL of ethanol was added to the recovered nanoparticles. The precipitated nanoparticles were dispersed with a vortex mixer and were centrifuged at a rotational speed of 5000 rpm for 5 minutes to recover crystal grains again. The operation of ethanol addition→centrifugation→recovery of nanoparticles was then repeated multiple times. High-purity nanoparticles thus recovered were dispersed in a nonpolar solvent chloroform to prepare a nonpolar nanoparticle dispersion liquid.

Subsequently, a series of steps including ultrasonic irradiation were performed by the same method and procedure as in Example 1 to prepare an aqueous nanoparticle dispersion of a sample No. 31 (In/Ga=0), a sample No. 32 (In/Ga=1), or a sample No. 33 (In/Ga=2).

[Sample Evaluation]

An emission spectrum and emission quantum yield of each of the sample No. 31 to the sample No. 33 were measured by the same method and procedure as in Example 1. An emission spectrum and emission quantum yield of each of the sample No. 32 and the sample No. 33 were also measured before the ultrasonic irradiation.

Figure 19:
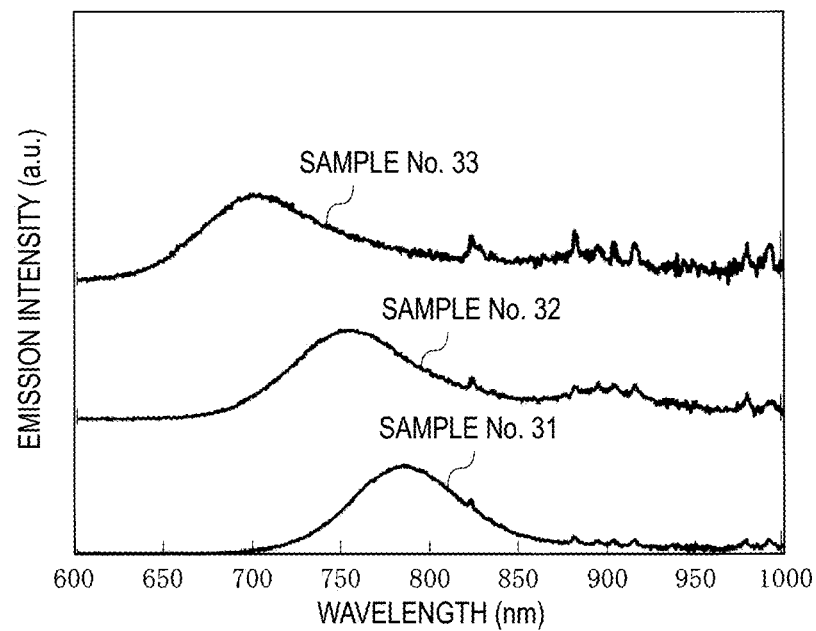
FIG. 19 is a profile of each emission spectrum of a sample No. 31 to a sample No. 33 in Example 3.
Figure 20:
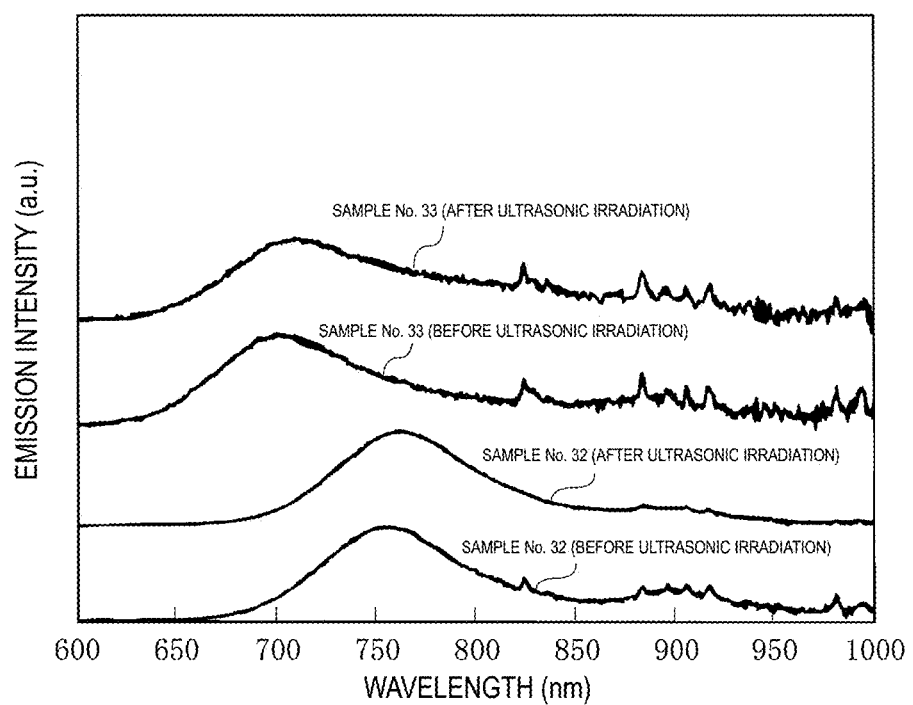
FIG. 20 is a profile of each emission spectrum before and after ultrasonic irradiation of the sample No. 32 and the sample No. 33 in Example 3.

FIG. 19 shows measurement results of emission spectra of the sample No. 31 to the sample No. 33 after the ultrasonic irradiation. FIG. 20 shows measurement results of emission spectra of the sample No. 32 and the sample No. 33 before and after the ultrasonic irradiation. In the figures, the horizontal axis represents the wavelength (nm), and the vertical axis represents the emission intensity (a.u).

Table 2 shows the emission intensity peak wavelength (nm), half-width ΔH, and emission quantum yield (%) of each of the sample No. 31 to the sample No. 33 before and after the ultrasonic irradiation.

TABLE 2

| Sample No. | Ga/In ratio | Peak wavelength (nm) | Half-width ΔH (nm) | Emission quantum yield (%) | |
|---|---|---|---|---|---|
| | | | | Before ultrasonic irradiation | After ultrasonic irradiation |
| 31 | 0 | 780 | 70 | 9 | 44 |
| 32 | 1 | 750 | 80 | 9 | 40 |
| 33 | 2 | 700 | 80 | 4 | 10 |

Table 2 and FIG. 19 show that the emission intensity peak wavelength is 780 nm in the sample No. 31, 750 nm in the sample No. 32, and 700 nm in the sample No. 33, and all these samples emit light in the near-infrared region. It was found that the emission intensity peak wavelength shifted toward the short wavelength side as the blending ratio of Ga to In, that is, the Ga/In ratio increased, and the peak wavelength can be controlled in accordance with the Ga content.

Table 2 and FIG. 20 show that at a constant Ga/In ratio the peak wavelength and half-width ΔH were not changed by the ultrasonic irradiation, but the emission quantum yield was 9%, 9%, or 4% before the ultrasonic irradiation and 44%, 40%, or 10% after the ultrasonic treatment, which is at least 2.5 times the emission quantum yield before the ultrasonic irradiation.

Next, absorption spectra of the sample No. 31 to the sample No. 33 were measured by the same method and procedure as in Example 1.

Figure 21:
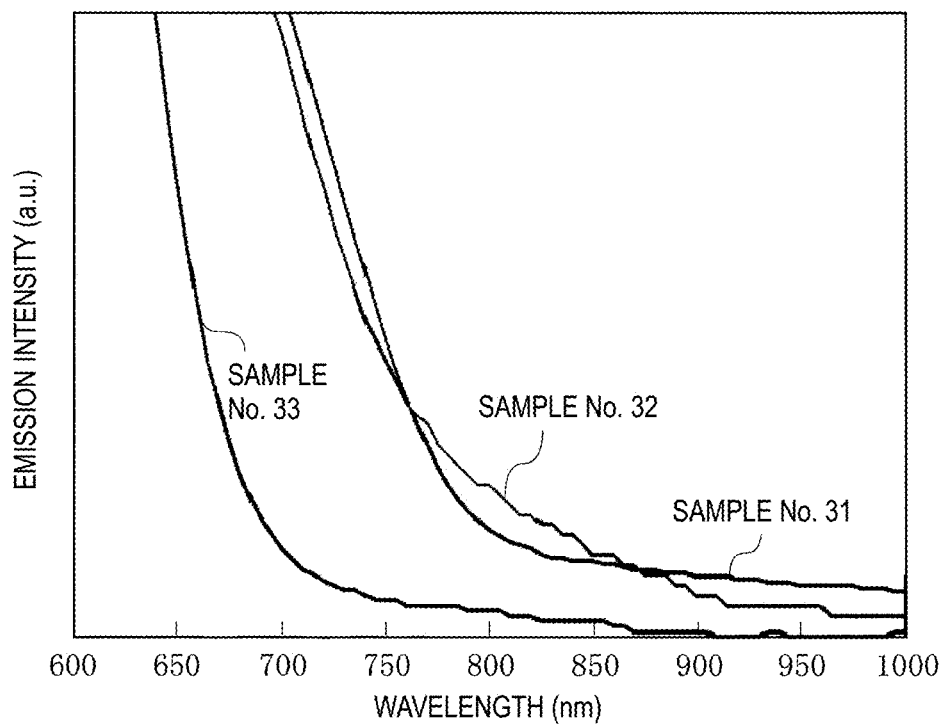
FIG. 21 is a profile of each absorption spectrum of the sample No. 31 to the sample No. 33 in Example 3.

FIG. 21 shows the measurement results. The horizontal axis represents the wavelength (nm), and the vertical axis represents the absorbance (a.u.).

As is clear from FIG. 21, the absorption edge wavelength shifts to the short wavelength side as the Ga content increases, and the injection of the Ga component probably increases the band gap.

Thus, it was found that although the injection of the Ga component into the AgInSe compound semiconductor shifts the peak wavelength to the short wavelength side in accordance with the Ga content, ultrasonication can improve the luminous efficiency while maintaining the emission wavelength and the half-width ΔH.

Example 4

The sample No. 12 prepared in Example 1 was characterized by an in vivo imaging technique in contrast with a comparative example sample.

[Comparative Example Sample]

Qdot 800ITK carboxyl quantum dots (hereinafter referred to as "Qdot 800") manufactured by Invitrogen were used as a comparative example sample.

Qdot 800 includes nanoparticles with a core-shell structure, in which the core is composed of toxic Cd, Se, and Te, and the shell is composed of ZnS. The surface of the ZnS is covered with a polymer with a carboxylate group (—COO). Qdot 800 had an average particle size of approximately 15 nm. The comparative example sample Qdot 800 was designated as a sample No. 41.

The sample No. 41 had an emission quantum yield of 58% as measured by the same method and procedure as in Example 1. The sample No. 12 has an emission quantum yield of 44%, as described in Example 1.

An emission spectrum of the sample No. 41 was measured by the same method and procedure as in Example 1.

Figure 22:
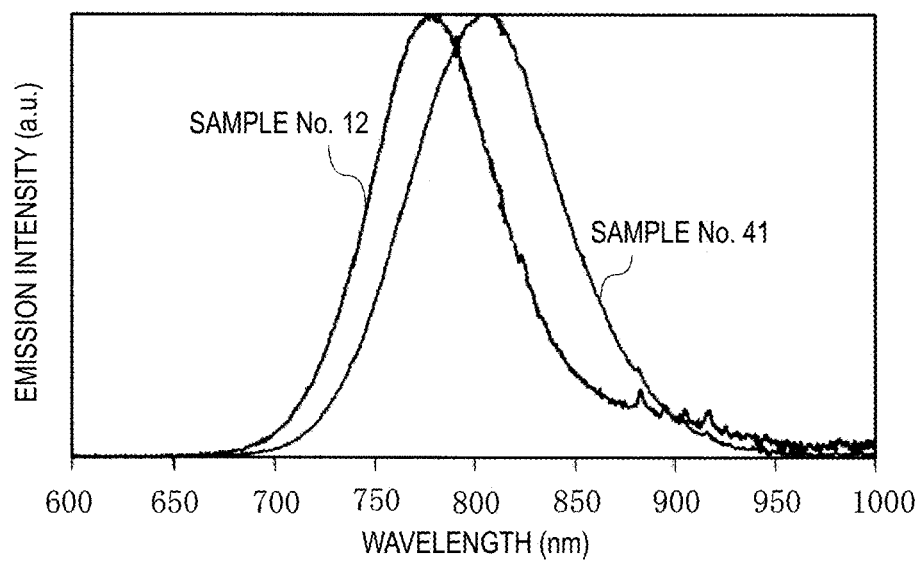
FIG. 22 is a profile of an emission spectrum of a sample No. 41 in Example 4 together with that of the sample No. 12.

FIG. 22 is a profile of the emission spectrum of the sample No. 41, compared with the emission spectrum of the sample No. 12 (FIG. 14). In the figure, the horizontal axis represents the wavelength (nm), and the vertical axis represents the emission intensity (a.u.).

As is clear from FIG. 22, the sample No. 41 has an emission intensity peak wavelength of approximately 800 nm and a half-width ΔH of 100 nm or less, which is slightly larger than that of the sample No. 12. Thus, it was confirmed that like the sample No. 12 the sample No. 41 also has a half-width ΔH within the scope of the present invention.

[Toxicity Evaluation]

R8 (octaarginine) manufactured by Sigma-Aldrich Corporation was used as a surface modifier. A mixed solution of the sample No. 12 and R8 and a mixed solution of the sample No. 41 and R8 were added to an ASCs culture fluid to evaluate toxicity to ASCs.

More specifically, first, a Dulbecco's modified Eagle's medium (hereinafter referred to as "DMEM") and a nutrient mixture Hams' F12 (hereinafter referred to as "F12") were prepared as a culture medium, a fetal bovine serum (hereinafter referred to as "FBS") was prepared as a supplement, and penicillin-streptomycin was prepared as an antibiotic. The DMEM, F12, FBS, and penicillin-streptomycin were all manufactured by Thermo Fisher Scientific Inc.

Then, a mixture of equal amounts of DMEM and F12 was used as a basal medium and was mixed with 20% FBS and 1% penicillin-streptomycin to prepare a culture medium.

The basal medium was mixed with 2% FBS and 1% penicillin-streptomycin to prepare an ASCs maintenance medium (hereinafter referred to simply as a "maintenance medium").

A 96-well plate (length×width: 8×12, volume per well: 360 μL) manufactured by Corning Inc. was prepared as a cell culture microplate.

Then, stem cells were separated and prepared from a mouse adipose tissue, were seeded in the 96-well plate at a cell number of $1 \times 10^4$ cells/well, and were cultured at a temperature of 37° C. for 24 hours in an incubator adjusted to a $CO_2$ concentration of 5% to prepare a first ASCs culture fluid.

Next, using the maintenance medium, R8 and the sample No. 12 or the sample No. 41 were mixed at a predetermined molar concentration of the sample No. 12 or the sample No. 41 and were allowed to stand for 30 minutes. More specifically, the sample No. 12 was diluted with the maintenance medium to a molar concentration in the range of 0 to 512 nmol/L to prepare a AgInSe solution. R8 was then diluted with the maintenance medium such that the mixing mole ratio of the sample No. 12 to R8 was 1:10000 to prepare an R8 solution. The AgInSe solution and the R8 solution were then mixed and allowed to stand for 30 minutes to prepare a sample No. 12a composed of a AgInSe-R8 mixed solution.

In the same manner, the sample No. 41 was diluted with the maintenance medium to a molar concentration in the range of 0 to 64 nmol/L to prepare a Qdot 800 solution R8 was then diluted with the maintenance medium such that the mixing mole ratio of Qdot 800 to R8 was 1:10000 to prepare an R8 solution. Then, the Qdot 800 solution and the R8 solution were mixed and allowed to stand for 30 minutes to prepare a sample No. 41a composed of a Qdot 800-R8 mixed solution.

Next, the first ASCs culture fluid was replaced with the sample No. 12a, and the sample No. 12a was cultured in the culture medium for 24 hours to prepare a second ASCs culture fluid. Likewise, the first ASCs culture fluid was replaced with the sample No. 41a, and the sample No. 41a was cultured in the culture medium for 24 hours to prepare a third ASCs culture fluid.

For the sample No. 12a and the sample No. 41a, a viable cell counting kit (Cell Counting Kit-8 manufactured by Dojindo Laboratories) was used to determine the cell survival rate, wherein the cell survival rate of an additive-free cell group was 100%.

Figure 23:
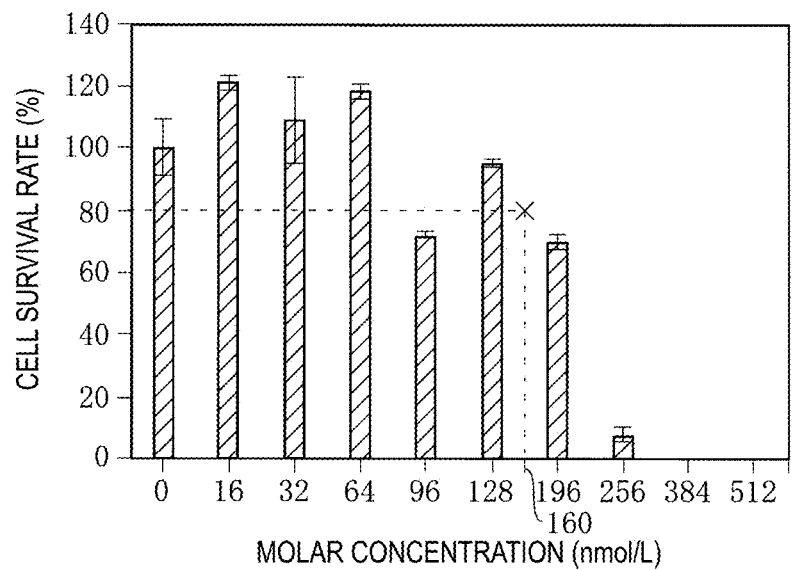
FIG. 23 is a view of the relationship between the molar concentration and the cell survival rate of a sample No. 12a in Example 4.
Figure 24:
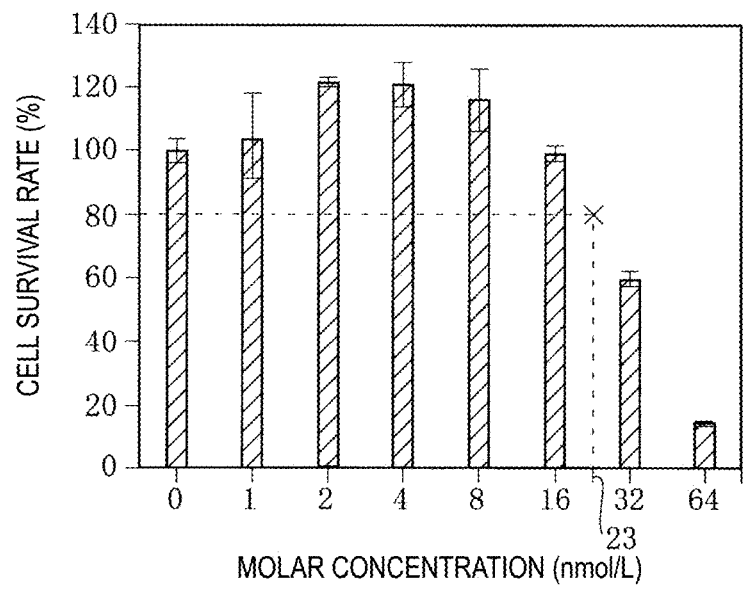
FIG. 24 is a view of the relationship between the molar concentration and the cell survival rate of a sample No. 41a in Example 4.

FIG. 23 shows the measurement results of the sample No. 12a, and FIG. 24 shows the measurement results of the sample No. 41a. In FIGS. 23 and 24, the horizontal axis represents the molar concentration (nmol/L), and the vertical axis represents the cell survival rate (%).

As is clear from FIGS. 23 and 24, the sample No. 41a had a cell survival rate of 80% or more at a molar concentration of 23 nmol/L or less, whereas the sample No. 12a could have a cell survival rate of 80% or more even at a molar concentration of 160 nmol/L. Thus, the sample No. 12a could be added at a concentration approximately seven times higher than that of the sample No. 41a. This is probably because the nanoparticles of the sample No. 41a contain toxic Cd, and therefore the addition of even a small amount of the sample No. 41a to cells kills many cells, whereas the nanoparticles of the sample No. 12a are formed of a low-toxic AISe compound semiconductor, and therefore even a molar concentration of the sample No. 12a much higher than that of the sample No. 41a can effectively prevent cell death and maintain a high cell survival rate.

Although the cell survival rate in FIGS. 23 and 24 exceeds 100% at some molar concentrations, and the cell survival rate in FIG. 23 is below 80% at a molar concentration of 96 nmol/L, these may result from factors such as variations in cell proliferation in each well of the 96-well plate and cell exhaustion. When the characteristics of the graphs of FIGS. 23 and 24 are viewed as a whole, however, the cell survival rate can be evaluated as described above.

[Fluorescence Intensity of Sample]

The sample No. 12 was diluted to a molar concentration of 160 nmol/L with phosphate-buffered saline (hereinafter referred to as "PBS") manufactured by Sigma-Aldrich Corporation, which is widely used as a cell washing solution. The sample No. 41 was also diluted with PBS to a molar concentration of 23 nmol/L.

The fluorescence intensity of each of these diluted sample No. 12 and sample No. 41 was measured with an IVIS spectrum CT manufactured by PerkinElmer, Inc. under the conditions of excitation light: 710 nm and detection filter wavelength: 800 nm.

Figure 25:
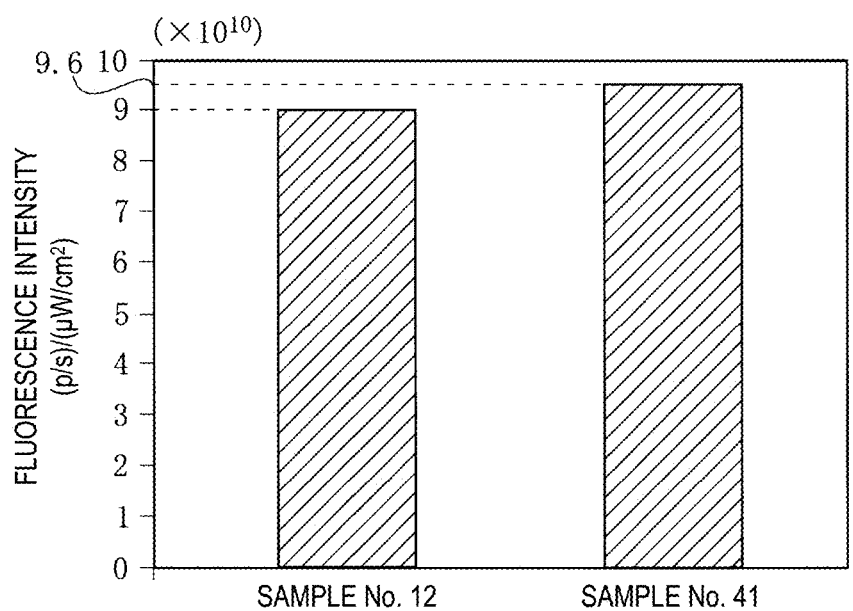
FIG. 25 is a view of fluorescence intensities of the sample No. 12 and the sample No. 41 in Example 4.

FIG. 25 shows the fluorescence intensity of each of the sample No. 12 and the sample No. 41. The vertical axis represents the fluorescence intensity $(p/s)/(\mu W/cm^2)$. Each fluorescence intensity represents a value obtained by subtracting the fluorescence intensity of the PBS alone, and the fluorescence of the light source itself is evaluated.

Thus, the fluorescence intensity was $9.0 \times 10^{10}$ $(p/s)/(\mu W/cm^2)$ in the sample No. 12 and $9.6 \times 10^{10}$ $(p/s)/(\mu W/cm^2)$ in the sample No. 41. Thus, the fluorescence intensity of the sample No. 12 corresponds to approximately 94% of the fluorescence intensity of the sample No. 41, and the sample No. 12, which is a sample of the present invention, had a sufficient fluorescence intensity comparable to that of the sample No. 41 (Qdot 800), which is a comparative example sample.

The sample No. 12 was then diluted with PBS to a molar concentration of 0 nmol/L, 20 nmol/L, 40 nmol/L, 80 nmol/L, and 160 nmol/L, and the diluted sample was subcutaneously injected into a predetermined portion of a mouse. The fluorescence intensity was then measured as described above with the IVIS spectrum CT under the conditions of excitation light: 710 nm and detection filter wavelength: 800 nm.

Figure 26:
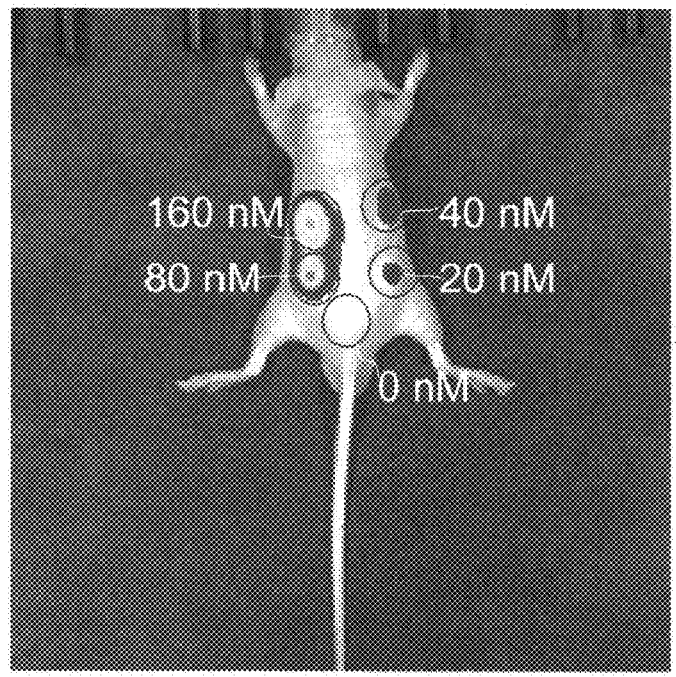
FIG. 26 is a view of the relationship between the molar concentration and the fluorescent state when a sample of the sample No. 12a is subcutaneously injected into a mouse in Example 4.

FIG. 26 is a photomicrograph showing the fluorescent state of the sample No. 12. In the figure, the O marks indicate a peripheral region to which a specified molar concentration of sample is added. The original image is a color image, and FIG. 26 shows a monochrome image into which the color image converted. In the original image, a region with a low fluorescence intensity is displayed in blue, a region with a high fluorescence intensity is displayed in yellow, and the intensity difference is displayed in multiple colors. In the converted monochrome image of FIG. 26, the intensity difference of the fluorescence intensity is displayed in shades of gray. In the figure, "mol/L" is simply expressed in "M".

As is clear from FIG. 26, without the sample No. 12, that is, when the molar concentration of the sample No. 12 is 0 nmol/L, no fluorescence is emitted, and when the molar concentration is 20 nmol/L or 40 nmol/L, the entire added region has a dark color tone, which indicates a low fluorescence intensity. In contrast, at a molar concentration of 80 nmol/L or 160 nmol/L, the peripheral portion has a dark color tone and a low fluorescence intensity, but the central portion has a light color tone and a high fluorescence intensity. This indicates a positive correlation between the molar concentration of the sample injected into the cell and the fluorescence intensity.

[Evaluation of Labeling Properties]

Using the above culture medium, $1 \times 10^5$ cells of ASCs were seeded in a 25-mL cell culture flask (manufactured by Corning Inc.) and were cultured at a temperature of 37° C. for 24 hours in an incubator adjusted to a $CO_2$ concentration of 5% to prepare a fourth ASCs culture medium. The sample No. 12 was then diluted with the maintenance medium to a molar concentration of 15 nmol/L to prepare a AgInSe solution. Furthermore, R8 was diluted with the maintenance medium such that the mole ratio of R8 to the sample No. 12 was 10000 to prepare an R8 solution. The AgInSe solution and the R8 solution were then mixed and allowed to stand for 30 minutes to prepare a sample No. 12b composed of a AgInSe-R8 mixed solution. Subsequently, the fourth ASCs culture fluid was replaced with the sample No. 12b, and the sample No. 12b was cultured for 24 hours to prepare a fifth ASCs culture fluid. Next, a trypsin-EDTA solution (manufactured by Sigma-Aldrich Corporation) was used to remove and recover the sample No. 12b from the cell. Then, $5 \times 10^4$ cells were diluted with PBS, and the fluorescence intensity of each of the sample No. 12b and PBS was measured with the IVIS spectrum CT under the conditions of excitation light: 710 nm and detection filter wavelength: 800 nm, as described above.

Figure 27:
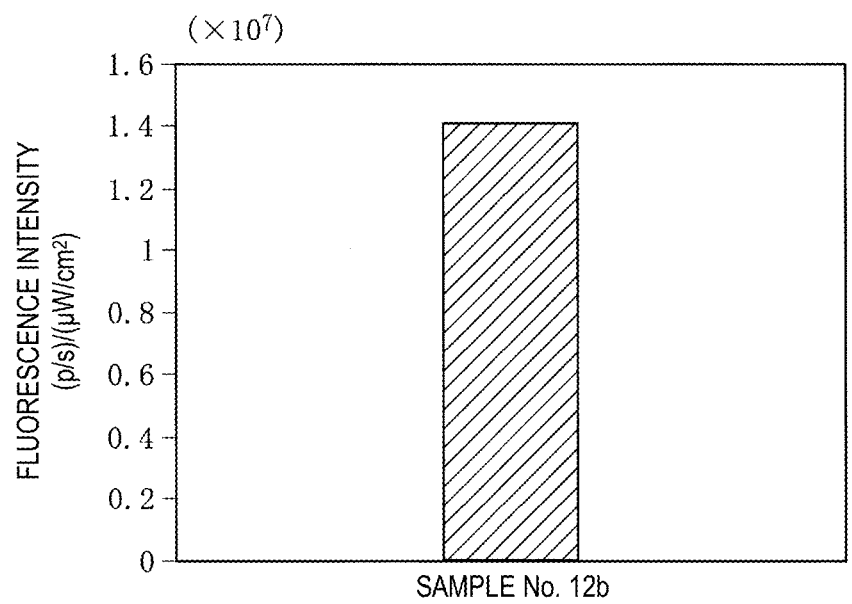
FIG. 27 is a view of the fluorescence intensity of a sample No. 12b in Example 4.

FIG. 27 shows the measurement result. The vertical axis represents the fluorescence intensity $(p/s)/(\mu W/cm^2)$, which is obtained by subtracting the fluorescence intensity of PBS alone from the sample No. 12b.

As is clear from FIG. 27, the sample No. 12b had a fluorescence intensity of $1.4 \times 10^7$ $(p/s)/(\mu W/cm^2)$, and the fluorescence of the AgInSe nanoparticles was observed. This indicates good labeling properties.

[Element Concentration of Sample]

Using the above culture medium, $7 \times 10^5$ cells of ASCs were seeded in the 25-mL cell culture flask and were cultured as described above to prepare a sixth ASCs culture medium. The sample No. 12 was then diluted with the maintenance medium to a molar concentration of 10 nmol/L to prepare a AgInSe solution. Furthermore, R8 was diluted with the maintenance medium such that the mole ratio of R8 to the sample No. 12 was 10000 to prepare an R8 solution. The AgInSe solution and the R8 solution were then mixed and allowed to stand for 30 minutes to prepare a sample No. 12c composed of a AgInSe-R8 mixed solution.

Subsequently, the sixth ASCs culture fluid was replaced with the sample No. 12c, and the sample No. 12c was cultured for 24 hours. Next, the trypsin-EDTA solution was used to remove and recover the sample No. 12c from the cell.

A sample No. 12d without surface modification with R8 was prepared by the same method and procedure as the sample No. 12c except that the AgInSe solution was not mixed with the R8 solution.

Furthermore, a sample No. 42 composed only of cells was prepared by the same method and procedure as the sample No. 12c except that the AgInSe-R8 mixed solution was not added.

The sample No. 12c, the sample No. 12d, and the sample No. 42 were then dispersed in water, and the element concentration was measured by inductively coupled plasma-mass spectrometry (ICP-MS).

Table 3 shows the measurement results.

TABLE 3

| Sample No. | Element concentration (mmol/L) | | | Note |
|---|---|---|---|---|
| | Zn | Ag | In | |
| 12c | 0.0046 | 0.0016 | 0.0049 | With R8 |
| 12d | 0.0033 | 0.0007 | 0.0019 | Without R8 |
| 42* | 0.0033 | <0.0001 | <0.0001 | Only cells |

*Outside the scope of the present invention

As is clear from Table 3, in the sample No. 42 composed only of cells, Ag and In were below the detection limit. By contrast, in the sample No. 12c and the sample No. 12d, which contained the AgInSe nanoparticles, Ag and In were detected. The element concentrations of Ag and In in the sample No. 12c surface-modified with R8 are 2.3 to 2.6 times the element concentrations of Ag and In in the sample No. 12d without surface modification with R8. Thus, it was confirmed that surface modification of the AgInSe nanoparticles with R8 can effectively introduce the AgInSe nanoparticles into cells.

Although Zn was detected in the sample No. 12c, the sample No. 12d, and the sample No. 42, a trace amount of Zn component contained as a cell component was probably detected.

A light-emitting body disclosed has an emission quantum yield of 10% or more, preferably 30% or more, emits strong light with a small half-width ΔH of 100 nm or less in the near-infrared region in the range of 650 to 1000 nm, and is dispersed in water. Furthermore, a biological material labeling agent with low toxicity suitable for a biomarker for bioimaging is provided.

REFERENCE SIGNS LIST 2 water
3, 32 light-emitting body
4 nanoparticle
5 film
6 first organic molecular film
7 second organic molecular film
8 surface protective agent
9 alkylthiol
10 fatty acid
11 nonpolar solvent
16 fatty acid aqueous solution
17 aqueous phase
18 nonpolar solvent phase
19 phase-separated solution
20 ultrasonic wave
31 surface modifier
34 cell

The invention claimed is:

1. A dispersion comprising: water; and
a light-emitting body dispersed in the water, the light-emitting body comprising:
a nanoparticle of a compound semiconductor containing at least a Ag component, an In component, and a Se component; and
a film with hydrophilicity on a surface of the nanoparticle,
wherein the light-emitting body has an emission quantum yield of 10% or more and/or an emission intensity peak wavelength in a range of 650 to 1000 nm and a half-width of 100 nm or less at the emission intensity peak wavelength, the film has a double structure having a first organic molecular film containing at least an alkylthiol and a second organic molecular film composed mainly of a fatty acid with a plurality of alkyl groups and the hydrophilicity is imparted by ultrasonic irradiation.

2. The dispersion according to claim 1, wherein the emission quantum yield is 50% or less.

3. The dispersion according to claim 1, wherein the alkylthiol is 1-dodecanethiol.

4. The dispersion according to claim 1, wherein the fatty acid is oleic acid.

5. The dispersion according to claim 1, wherein the alkyl groups of the fatty acid have a longer chain length than the alkyl group of the alkylthiol.

6. The dispersion according to claim 1, wherein the first organic molecular film contains a surface protective agent containing n-octyl thioglycolate.

7. The dispersion according to claim 1, wherein the first organic molecular film contains a surface protective agent containing 1-dodecanethiol.

8. The dispersion according to claim 1, wherein the emission quantum yield is 30% or more.

9. The dispersion according to claim 1, wherein the nanoparticle contains a Ga component.

10. The dispersion according to claim 1, wherein the light-emitting body has a transmittance of 90% or more in a wavelength range of 1000 to 1100 nm.

11. The dispersion according to claim 1, wherein the In component is contained in a larger amount than a stoichiometric composition.

12. The dispersion according to claim 1, wherein the film is covered with a surface modifier containing a cationic cell-penetrating peptide.

13. The dispersion according to claim 12, wherein the cell-penetrating peptide is octaarginine.

14. The dispersion according to claim 12, wherein the light-emitting body introduced into an adipose-derived stem cell at 160 nmol/L on a molar concentration basis has a cell survival rate of 80% or more.

15. A method for producing a dispersion, the method comprising:
preparing a nonpolar nanoparticle dispersion liquid in which nanoparticles of a compound semiconductor containing at least a Ag component, an In component, and a Se component are dispersed in a nonpolar solvent;
preparing a precursor dispersion liquid by adding organic molecules including at least an alkylthiol to the nonpolar nanoparticle dispersion liquid to form a first organic molecular film on a surface of each nanoparticle;
preparing a fatty acid aqueous solution in which a fatty acid with a plurality of alkyl groups is dissolved in water in the presence of an alkali;

mixing the precursor dispersion liquid and the fatty acid aqueous solution to prepare a phase-separated solution containing a nonpolar solvent phase and an aqueous phase;

applying ultrasonic waves to the phase-separated solution to form a film with hydrophilicity on a surface of each nanoparticle; and dispersing the nanoparticles in water to prepare an aqueous nanoparticle dispersion.

16. The method for producing a dispersion according to claim 15, wherein the forming of the film on the surface of each nanoparticle includes forming an oil-in-water microemulsion by the ultrasonic irradiation so as to confine the nanoparticles with the first organic molecular film formed thereon and the fatty acid in the microemulsion to adsorb the fatty acid on the surface of each nanoparticle.

17. The method for producing a dispersion according to claim 15, wherein the preparing of the nonpolar nanoparticle dispersion liquid includes:

dissolving a Ag compound and an In compound in a solvent to prepare a Ag—In solution;

dissolving a Se powder in a solvent to prepare a Se solution;

injecting the Se solution into the Ag—In solution while the Ag—In solution is heated to a predetermined temperature to prepare a mixed solution; and heating the mixed solution at a reaction temperature higher than the predetermined temperature for a predetermined reaction time to produce a nanoparticle of a compound semiconductor covered with a surface protective agent.

18. The method for producing a dispersion according to claim 15, wherein the preparing of the nonpolar nanoparticle dispersion liquid includes:

dissolving a Ag compound, an In compound, and a Ga compound in a solvent to prepare a Ag—In—Ga solution;

dissolving a Se powder in a solvent to prepare a Se solution;

injecting the Se solution into the Ag—In—Ga solution while the Ag—In—Ga solution is heated to a predetermined temperature to prepare a mixed solution; and heating the mixed solution at a reaction temperature higher than the predetermined temperature for a predetermined reaction time to produce a nanoparticle of a compound semiconductor covered with a surface protective agent.

19. The method for producing a dispersion according to claim 15, further comprising mixing the nanoparticles with the film formed thereon and a surface modifier comprising a cationic cell-penetrating peptide so as to cover a surface of the film with the surface modifier.

20. The method for producing a dispersion according to claim 19, wherein the cell-penetrating peptide is octaarginine.

21. A biological material labeling agent comprising the dispersion according to claim 1.

* * * * *